(12) United States Patent
Faulhaber et al.

(10) Patent No.: US 11,564,808 B2
(45) Date of Patent: Jan. 31, 2023

(54) EXPANDABLE INTERVERTEBRAL IMPLANTS AND METHODS OF INSTALLATION THEREOF

(71) Applicant: GLOBUS MEDICAL, INC., Audubon, PA (US)

(72) Inventors: Kurt Faulhaber, Renton, WA (US); Mark Miccio, Lynbrook, NY (US); Prem Ramakrishnan, Trappe, PA (US)

(73) Assignee: Globus Medical, Inc., Audubon, PA (US)

(*) Notice: Subject to any disclaimer, the term of this patent is extended or adjusted under 35 U.S.C. 154(b) by 225 days.

(21) Appl. No.: 17/121,939

(22) Filed: Dec. 15, 2020

(65) Prior Publication Data

US 2021/0121301 A1    Apr. 29, 2021

Related U.S. Application Data

(63) Continuation of application No. 16/010,896, filed on Jun. 18, 2018, now Pat. No. 10,864,087, which is a continuation of application No. 15/729,211, filed on Oct. 10, 2017, now Pat. No. 10,022,241, which is a continuation of application No. 14/712,434, filed on May 14, 2015, now Pat. No. 9,814,602.

(51) Int. Cl.
*A61F 2/44*    (2006.01)

(52) U.S. Cl.
CPC ............ *A61F 2/447* (2013.01); *A61F 2/4455* (2013.01)

(58) Field of Classification Search
CPC .......... A61F 2/44; A61F 2/442; A61F 2/4425; A61F 2/4455; A61F 2/446; A61F 2/4465; A61F 2/447; A61F 2002/443; A61F 2002/4475
See application file for complete search history.

(56) References Cited

U.S. PATENT DOCUMENTS

| | | | | |
|---|---|---|---|---|
| 5,658,335 A * | 8/1997 | Allen | ............... | A61F 2/44 606/247 |
| 6,395,031 B1 * | 5/2002 | Foley | ............... | A61F 2/4465 623/908 |
| 6,685,742 B1 * | 2/2004 | Jackson | ............... | A61F 2/447 623/17.11 |
| 6,723,126 B1 * | 4/2004 | Berry | ............... | A61F 2/4611 606/247 |
| 6,730,126 B2 * | 5/2004 | Boehm, Jr. | ............... | A61F 2/447 623/17.15 |
| 7,678,148 B2 * | 3/2010 | Peterman | ............... | A61F 2/4455 623/17.11 |
| 7,883,542 B2 * | 2/2011 | Zipnick | ............... | A61B 17/320016 623/17.11 |
| 8,128,700 B2 * | 3/2012 | Delurio | ............... | A61F 2/4644 623/17.11 |
| 8,273,129 B2 * | 9/2012 | Baynham | ............... | A61F 2/447 623/17.16 |

(Continued)

FOREIGN PATENT DOCUMENTS

JP    2014531921 A    12/2014
WO    WO-2015087285 A1 * 6/2015 ........... A61F 2/4425

*Primary Examiner* — Eric S Gibson

(57) ABSTRACT

Embodiments herein are generally directed to expandable spinal implants, systems, apparatuses, and components thereof that can be used in spinal fusion and/or stabilization procedures, as well as methods of installation. The expandable spinal implants may be configured for lateral insertion.

16 Claims, 16 Drawing Sheets

(56) References Cited

U.S. PATENT DOCUMENTS

| | | | | |
|---|---|---|---|---|
| 8,409,291 B2* | 4/2013 | Blackwell | | A61F 2/4455 623/17.15 |
| 8,663,329 B2* | 3/2014 | Ernst | | A61F 2/442 623/17.15 |
| 8,685,095 B2* | 4/2014 | Miller | | A61F 2/4611 623/17.11 |
| 9,271,777 B2* | 3/2016 | Nichols | | A61B 17/88 |
| 9,370,433 B1* | 6/2016 | Morris | | A61F 2/442 |
| 9,445,919 B2* | 9/2016 | Palmatier | | A61F 2/447 |
| 9,655,740 B1* | 5/2017 | Faulkner | | A61B 17/025 |
| 9,737,411 B2* | 8/2017 | Loebl | | A61F 2/4455 |
| 9,795,493 B1* | 10/2017 | Bannigan | | A61F 2/4455 |
| 9,814,602 B2* | 11/2017 | Faulhaber | | A61F 2/4455 |
| 10,022,241 B2* | 7/2018 | Faulhaber | | A61F 2/4611 |
| 10,864,087 B2* | 12/2020 | Faulhaber | | A61F 2/447 |
| 2002/0107574 A1* | 8/2002 | Boehm, Jr. | | A61F 2/4611 623/17.16 |
| 2005/0283248 A1* | 12/2005 | Gordon | | A61F 2/4405 623/17.11 |
| 2006/0030943 A1* | 2/2006 | Peterman | | A61F 2/447 623/17.11 |
| 2006/0247778 A1* | 11/2006 | Ferree | | A61F 2/4425 623/23.61 |
| 2009/0088852 A1* | 4/2009 | Chee | | A61F 2/4611 623/17.11 |
| 2010/0185291 A1* | 7/2010 | Jimenez | | F16F 1/025 623/17.16 |
| 2011/0112644 A1* | 5/2011 | Zilberstein | | A61F 2/4611 623/17.15 |
| 2011/0172774 A1* | 7/2011 | Varela | | A61F 2/447 623/17.16 |
| 2012/0029637 A1* | 2/2012 | Ragab | | A61F 2/447 623/17.11 |
| 2012/0059474 A1* | 3/2012 | Weiman | | A61F 2/4611 623/17.16 |
| 2012/0185049 A1* | 7/2012 | Varela | | A61F 2/447 623/17.16 |
| 2012/0215316 A1* | 8/2012 | Mohr | | A61F 2/442 623/17.16 |
| 2012/0226357 A1* | 9/2012 | Varela | | A61F 2/447 623/17.16 |
| 2012/0259416 A1* | 10/2012 | Blackwell | | A61F 2/4455 623/17.16 |
| 2012/0271422 A1* | 10/2012 | Miller | | A61F 2/447 623/17.16 |
| 2012/0310350 A1* | 12/2012 | Farris | | A61F 2/4455 623/17.16 |
| 2013/0158664 A1* | 6/2013 | Palmatier | | A61F 2/4425 623/17.16 |
| 2013/0158668 A1* | 6/2013 | Nichols | | A61B 17/56 623/17.16 |
| 2013/0190876 A1* | 7/2013 | Drochner | | A61F 2/4455 623/17.16 |
| 2013/0197642 A1* | 8/2013 | Ernst | | A61F 2/442 623/17.16 |
| 2013/0211526 A1 | 8/2013 | Alheidt et al. | | |
| 2014/0277489 A1* | 9/2014 | Davenport | | A61F 2/4611 623/17.16 |
| 2015/0012098 A1* | 1/2015 | Eastlack | | A61F 2/442 623/17.15 |
| 2015/0018951 A1* | 1/2015 | Loe | | A61F 2/4425 623/17.15 |
| 2015/0094813 A1* | 4/2015 | Lechmann | | A61F 2/447 623/17.15 |
| 2015/0182347 A1* | 7/2015 | Robinson | | A61F 2/447 623/17.15 |
| 2015/0257894 A1* | 9/2015 | Levy | | A61F 2/442 623/17.15 |
| 2016/0015522 A1* | 1/2016 | Arnin | | A61F 2/447 623/17.15 |
| 2016/0051373 A1* | 2/2016 | Faulhaber | | A61F 2/44 623/17.16 |
| 2016/0051374 A1* | 2/2016 | Faulhaber | | A61B 17/8023 623/17.15 |
| 2016/0331542 A1* | 11/2016 | Faulhaber | | A61F 2/4611 |
| 2016/0338846 A1* | 11/2016 | Walker | | A61F 2/4611 |
| 2016/0354211 A1* | 12/2016 | Packer | | A61F 2/4611 |
| 2017/0056200 A1* | 3/2017 | Koch | | A61F 2/44 |
| 2017/0128226 A1* | 5/2017 | Faulhaber | | A61F 2/30767 |
| 2017/0172758 A1* | 6/2017 | Field | | A61F 2/4611 |
| 2018/0042731 A1* | 2/2018 | Bannigan | | A61F 2/447 |
| 2018/0085229 A1* | 3/2018 | Faulhaber | | A61F 2/447 |
| 2018/0296360 A1* | 10/2018 | Faulhaber | | A61F 2/4611 |
| 2021/0121301 A1* | 4/2021 | Faulhaber | | A61F 2/447 |

* cited by examiner

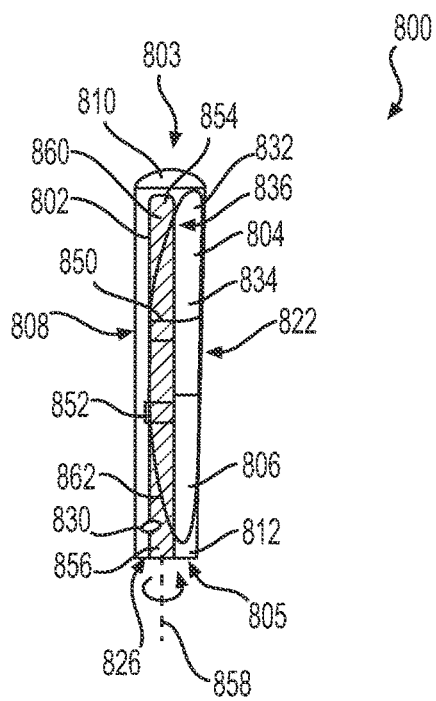 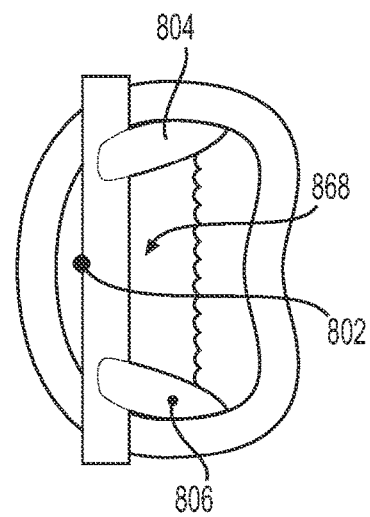
FIG. 8A  FIG. 8B
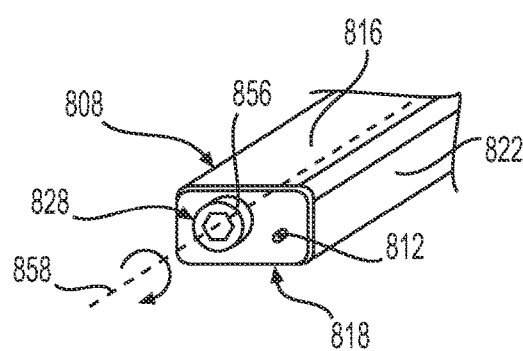 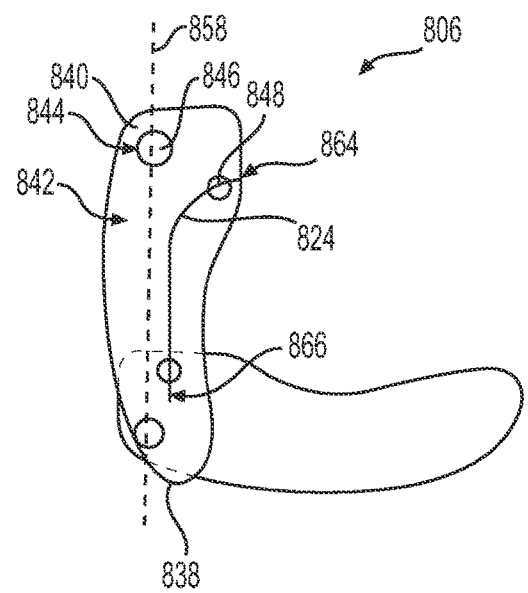
FIG. 8C  FIG. 8D

EXPANDABLE INTERVERTEBRAL IMPLANTS AND METHODS OF INSTALLATION THEREOF

CROSS REFERENCE TO RELATED APPLICATIONS

The present application is a continuation application of U.S. patent application Ser. No. 16/010,896, filed on Jun. 18, 2018, which is a continuation application of U.S. patent application Ser. No. 15/729,211, filed on Oct. 10, 2017 (published as U.S. Patent Publication No. US 2018-0085229), which is a continuation application of U.S. patent application Ser. No. 14/712,434, filed May 14, 2015, now issued as U.S. Pat. No. 9,814,602. The disclosures of all of which are being incorporated herein by reference in their entirety.

FIELD OF THE INVENTION

The present disclosure relates to expandable intervertebral devices and methods used to install these devices.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. One example of a spinal irregularity that may result from disc degeneration is spinal stenosis, the narrowing of a spinal canal, which can result in the compression of spinal nerves such as the spinal cord or cauda equina. In turn, the nerve compression can result in pain, numbness, or weakness. Other examples of conditions that can result from disc degeneration are osteoarthritis and disc herniation.

Often, these irregularities can be treated by performing a discectomy and/or immobilizing a portion of the spine. For example, treatment can include a surgical procedure that involves removal and replacement of an affected intervertebral disc with a prosthesis and the subsequent fusion of adjacent vertebrae. The prosthesis, such as an interbody cage or spacer, may be used either alone or in combination with one or more additional devices such as rods, screws, and/or plates.

SUMMARY OF THE INVENTION

Some embodiments herein are directed to an expandable spinal implant that can include a stationary base member comprising an elongate slot, the elongate slot having a longitudinal axis parallel to a longitudinal axis of the primary base member; a movable base member comprising an angled slot, the angled slot having a longitudinal axis that intersects a longitudinal axis of the movable base member; at least one guide member comprising a first end configured to be reversibly received within the primary base member and a second end configured to be received within the movable base member; and an actuator comprising a first arm configured to slideably engage the elongate slot and a second arm configured to slideably engage the angled slot.

Other embodiments herein are directed to an expandable spinal implant that can include a primary base member comprising an elongate slot, the elongate slot comprising an axis that is parallel to at least a portion of an inner side wall of the primary base member; a movable base member comprising an angled slot, the angled slot comprising an axis that intersects an inner side wall of the movable base member; at least one guide member comprising a first end configured to be reversibly received within the movable base member and a second end configured to be received within the stationary base member; and an actuator comprising a first arm configured to slideably engage the elongate slot and a second arm configured to slideably engage the angled slot.

Yet other embodiments herein are directed to an expandable spinal implant that can include a primary base member comprising a leading end, a trailing end, and a length therebetween, and further comprising an elongate slot extending at least partially along the length thereof, wherein the elongate slot extends parallel to the length of the primary base member; a movable base member comprising a leading end, a trailing end, and a length therebetween, and further comprising an angled slot extending at least partially along the length thereof, wherein the angled slot intersects at least one side surface of the movable base member; at least one guide member comprising a first end configured to be reversibly received within the movable base member and a second end configured to be received within the stationary base member; and an actuator comprising a first arm configured to slideably engage the elongate slot and a second arm configured to slideably engage the angled slot.

Some embodiments herein are directed to an expandable spinal implant that can include an elongate body comprising a leading end and a trailing end; an actuator housed within the elongate body; a translatable connector configured to engage the actuator and translate relative thereto; a leading arm pivotably coupled to the connector and slideably coupled to the leading end of the elongate body; and a trailing arm pivotably coupled to the leading arm and slideably coupled to the trailing end of the elongate body.

Other embodiments herein are directed to an expandable spinal implant that can include an elongate body comprising a first end and a second end; a first arm pivotably and translationally coupled to the elongate body at the first end; and a second arm pivotably and translationally coupled to the elongate body at the second end; wherein the first and second arms are hingedly coupled to each other.

Yet other embodiments herein are directed to an expandable spinal implant that can include an elongate body comprising a first end and a second end; a first arm having a lateral end and a medial end, wherein the lateral end of the first arm is pivotably and translationally coupled to the first end of the elongate body; and a second arm having a lateral end and a medial end, wherein the lateral end of the second arm is pivotably and translationally coupled to the second end of the elongate body; wherein the medial ends of the first and second arms are hingedly coupled to each other; and wherein the medial ends of the first and second arms are configured to reversibly pivot towards and away from the elongate body.

Some embodiments herein are directed to an elongate body having a first end and a second end; a first arm comprising a lateral end and a medial end, wherein the medial end of the first arm is coupled with the first end of the elongate body; and a second arm comprising a lateral end and a medial end, wherein the medial end of the second arm is coupled with the second end of the elongate body.

Other embodiments herein are directed to an expandable spinal implant that can include a first elongate body having a leading end and a trailing end; a second elongate body having a leading end and a trailing end; a first arm comprising a proximal end and a distal end, wherein the distal end is pivotably coupled to the first elongate body; a second arm comprising a proximal end and a distal end, wherein the distal end is pivotably coupled to the second elongate body and the proximal end is rotatably engaged with the first arm; and a linearly-translatable actuator pivotably coupled to the proximal ends of the first and second arms.

Still other embodiments herein are directed to an expandable spinal implant that can include a first elongate body comprising a leading end and a trailing end; a second elongate body comprising a leading end and a trailing end; and a first expansion assembly, comprising a first ramp member configured to slideably engage the first elongate body, a second ramp member configured to slideably engage the second elongate body, and a wedge member configured to slideably engage the first and second ramp members.

Further areas of applicability of the present disclosure will become apparent from the detailed description provided hereinafter. It should be understood that the detailed description and specific examples, while indicating certain embodiments, are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIGS. 8A-8D illustrate another embodiment of an expandable spinal implant.

DETAILED DESCRIPTION

Figure 1:
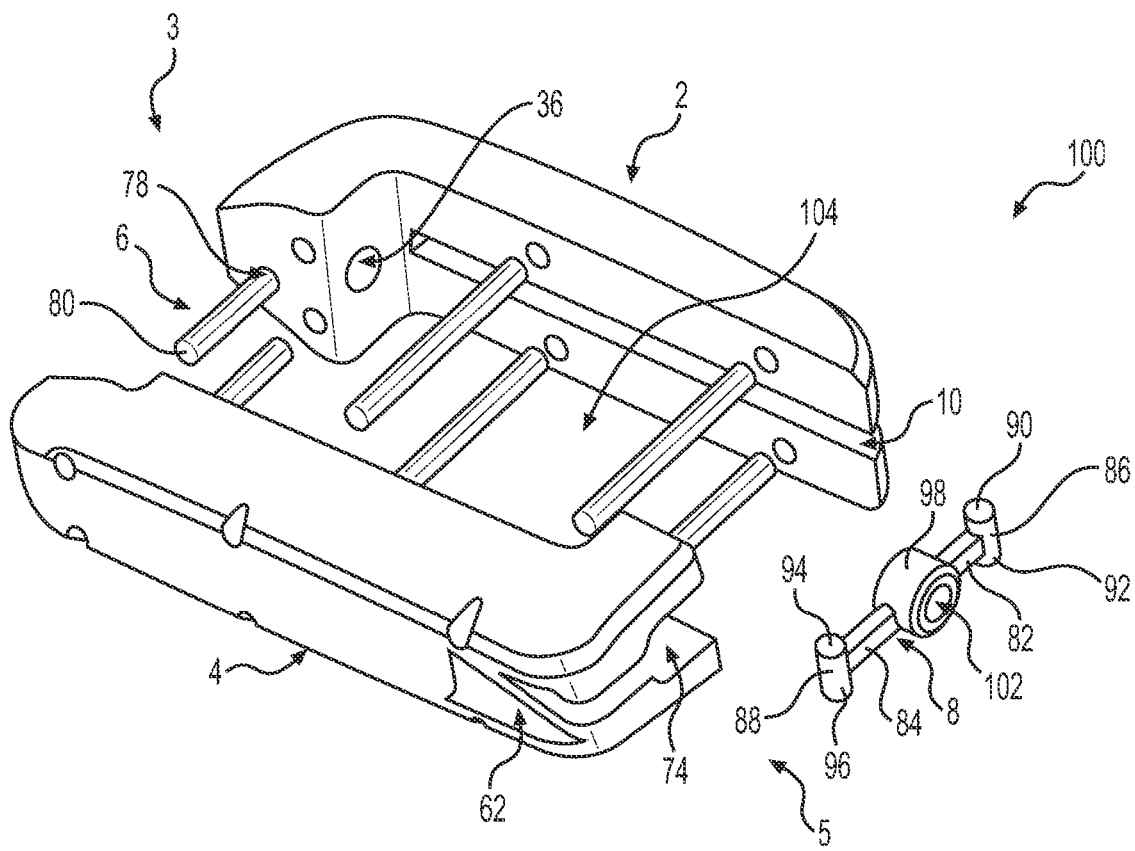
FIG. 1 illustrates a perspective view of one embodiment of an expandable spinal implant described herein.

In a spinal fusion procedure, the intervertebral disc space can be accessed via various approaches (e.g., anterior, posterior, transforaminal, and/or lateral). In a lateral procedure, a prosthesis may be inserted through an incision on a patient's side; advantageously, this type of approach may generally avoid muscles and nerves that may otherwise be encountered in an anterior, posterior, and/or transforaminal approach. Disclosed herein are expandable spinal implants that can be configured for use in lateral lumbar interbody fusion (LLIF) procedures, and that may be referred to as expandable lateral spinal implants. For example, the expandable spinal implants may each have a length (e.g., as measured between the leading and trailing ends) that is about 100-300% greater than a width thereof (e.g., as measured in the anterior-posterior direction). The expandable implants may also each have a length that is configured to laterally span a vertebral endplate. For example, the expandable spinal implants may each have a length in the range of from about 40 mm to about 60 mm. In some embodiments, the expandable implant may have a constant (e.g., static and/or unexpandable) length. The expandable spinal implants described herein may have a variable width and may be configured to collapse to a smaller width prior to insertion and/or expand to a larger width after insertion. For example, some spinal implants described herein may have a collapsed width in the range of from about 15 mm to about 30 mm, and an expanded width in the range of from about 20 mm to about 35 mm. Other spinal implants described herein may have a collapsed width in the range of from about 10 mm to about 15 mm, and an expanded width in the range of from about 25 mm to about 30 mm. Accordingly, these spinal implants may be configured for use in minimally-invasive surgery (MIS). For example, they may be inserted through a relatively small incision (e.g., 10-30% narrower), reducing trauma to the patient. Additionally, these spinal implants may be inserted laterally in the far anterior side of the intervertebral space, thereby minimizing interference with the lumbar plexus. Conversely, the expandable spinal implants described herein may be configured to expand to a width greater than that of other implants in the art (e.g., 15-40% greater), without requiring a larger incision. Accordingly, the expandable spinal implants of the present disclosure may be configured to more evenly distribute the vertebral load, increase surface area contact with the vertebral endplates, engage bone adjacent the apophyseal ring, reduce or inhibit cage subsidence, and/or promote increased fusion by being configured to receive a greater amount of biomaterials, without increasing trauma to the patient.

Components of all of the systems and devices disclosed herein can be made of materials known to those skilled in the art, including metals (e.g., titanium), metal alloys (e.g., stainless steel, titanium alloys, and/or cobalt-chromium alloys), ceramics, polymers (e.g., poly ether ether ketone (PEEK), polyphenylene sulfone (PPSU), polysulfone (PSU), polycarbonate (PC), polyetherimide (PEI), polypropylene (PP), polyacetals, or mixtures or co-polymers thereof), allograft, and/or combinations thereof. In some embodiments, the systems and devices may include radiolucent and/or radiopaque materials. In other embodiments, one or more components may be coated with a bone growth-enhancing material, such as hydroxyapatite. The components can also be machined and/or manufactured using techniques known to those skilled in the art. For example, polymeric components may be injection-molded or blow-molded. Additionally, the devices disclosed herein may be used together with materials that encourage bone growth, such as bone graft material, demineralized bone matrix, bone chips, and/or bone morphogenetic proteins. In some embodiments, these materials may advantageously be packed into hollow areas of the devices described herein.

As described herein, the spinal implants of the present disclosure may be configured for placement between two adjacent vertebrae, for example, as part of a spinal fusion procedure. These spinal implants may be referred to as, without limitation, interbody spacers, interbody fusion devices, interbody cages, and/or intervertebral cages. Each of the spinal implants described herein may include superior and/or inferior surfaces that are configured to engage and/or contact a vertebral endplate or other vertebral surface. In some embodiments, the superior and/or inferior surfaces may be convex, corresponding to the topography of the endplates. Additionally, the superior and/or inferior surfaces of each of the spinal implants described herein may include one or more texturizing members. Examples of such texturizing members include, but are not limited to, projections, bumps, teeth, grooves, peaks, spikes, and/or knurling. These texturizing features may advantageously enhance the interaction or fiction, and/or reduce movement, between the implant and the vertebrae. Those skilled in the art may appreciate that directional terms such as "anterior," "posterior," "superior," "inferior," "top," and "bottom," and the like may be used herein for descriptive purposes and do not limit the orientation(s) in which the devices may be used. For example, those skilled in the art may appreciate that, in use, a "superior" surface may be installed adjacent an inferior vertebra, and vice versa. Accordingly, a feature described as being on top may actually be oriented towards the bottom after installation.

Turning now to FIGS. 1-4G, some embodiments herein are directed to an expandable spinal implant 100 that can include a first (e.g., primary and/or stationary) base member 2, a second (e.g., movable) base member 4, at least one guide member 6, and an actuator 8. The implant 100 may include a leading end 3 and a trailing end 5. As described further herein, the movable base member 4 may be configured to move (e.g., translate) relative to the primary base member 2, or vice versa. The expandable spinal implant 100 may advantageously be configured to transition between an expanded configuration and a collapsed configuration, wherein the implant 100 has a width, as measured between an outer side surface of the primary base member 2 and an outer side surface of the movable base member 4, that is greater in the expanded configuration than in the collapsed configuration. In some embodiments, the expandable spinal implant 100 may have a collapsed width in the range of from about 15 mm to about 30 mm, and an expanded width in the range of from about 20 mm to about 35 mm. The primary and movable base members 2, 4 may define an expandable window 104 therebetween. The expandable window 104 may be configured to receive a fusion-enhancing material or other biomaterial, as described herein.

Figure 2A:
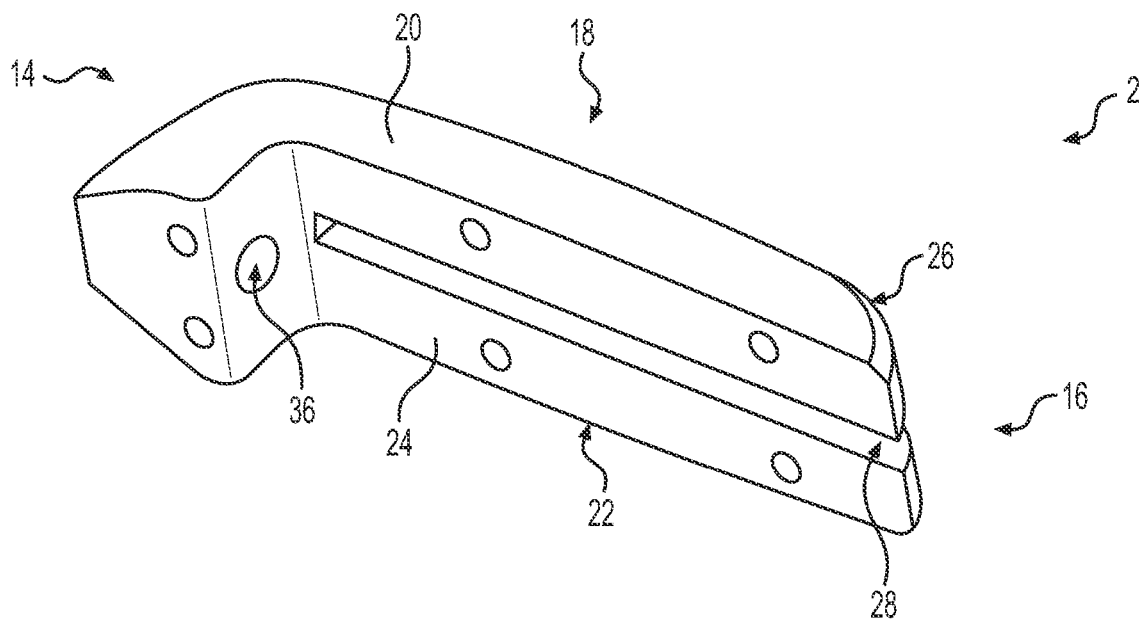
FIG. 2A illustrates a perspective view of one embodiment of a primary base member described herein.

As illustrated in FIG. 2A, the primary base member 2 can include a leading end 14, a trailing end 16, and a side wall 18 therebetween. The primary base member 2 may have a length as measured between the leading end 14 and the trailing end 16. Although not limited to any particular orientation, in some embodiments the side wall 18 may be configured to be oriented anteriorly in a patient and may thus be referred to as an anterior side wall. The primary base member 2 can also include a superior surface 20, an inferior surface 22, an inner side surface 24, and an outer side surface 26. In some embodiments, the outer side surface 26 may be convex, as viewed from the superior and/or inferior surfaces 20, 22. The superior and inferior surfaces 20, 22 may be convex, as viewed from the outer side surface 26, leading end 14, and/or trailing end 16. As described herein, the superior and/or inferior surfaces 20, 22 may include a plurality of texturizing members.

Figure 2B:
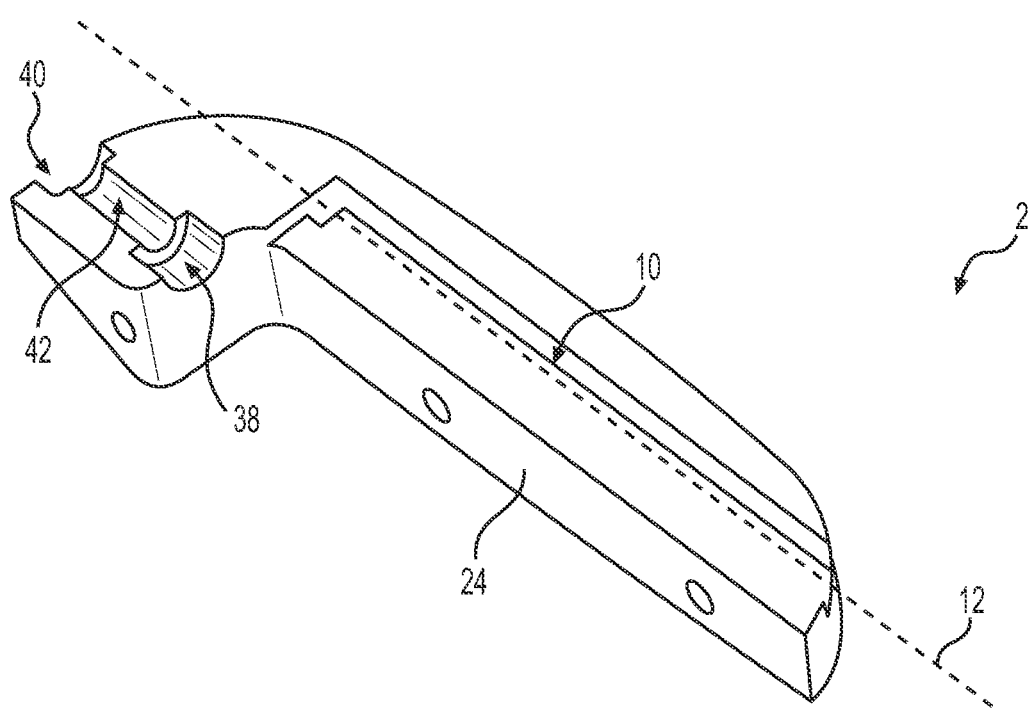
FIGS. 2B-D illustrate cross-sectional views of one embodiment of a primary base member described herein.
Figure 2C:
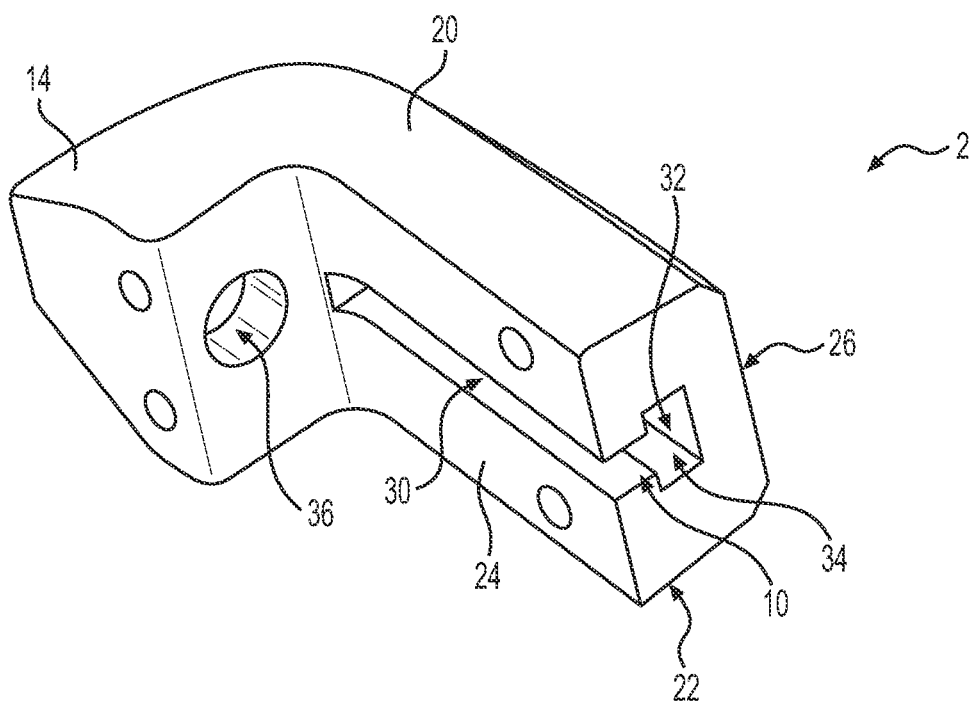

As illustrated in FIGS. 2B-C, the primary base member 2 can include an elongate slot 10. As illustrated in FIG. 2B, the elongate slot 10 can include a longitudinal axis 12 and can extend in a straight line and/or at least partially along a length of the primary base member 2. Accordingly, the longitudinal axis 12 of the elongate slot 10 may be parallel to the length and/or a longitudinal axis 13 of the primary base member 2, as illustrated in FIG. 2B. The longitudinal axis 12 may be parallel to at least a portion of the inner side surface 24, as illustrated in FIG. 2B. As illustrated in FIG. 2A, the elongate slot 10 can include an opening 28 that extends along the inner side surface 24 of the primary base member 2. The opening 28 may also extend at least partially along the trailing end 16 of the primary base member 2, as illustrated in FIG. 2A. As illustrated in FIG. 2C, the elongate slot 10 can include a main passageway 30 and a supplemental passageway, the supplemental passageway including first and second corridors 32, 34. The first and second corridors 32, 34 may each extend in opposite directions at a 90 degree angle away from the main passageway 30. Accordingly, the elongate slot 10 can include a T-shaped transverse cross-section.

Figure 2D:
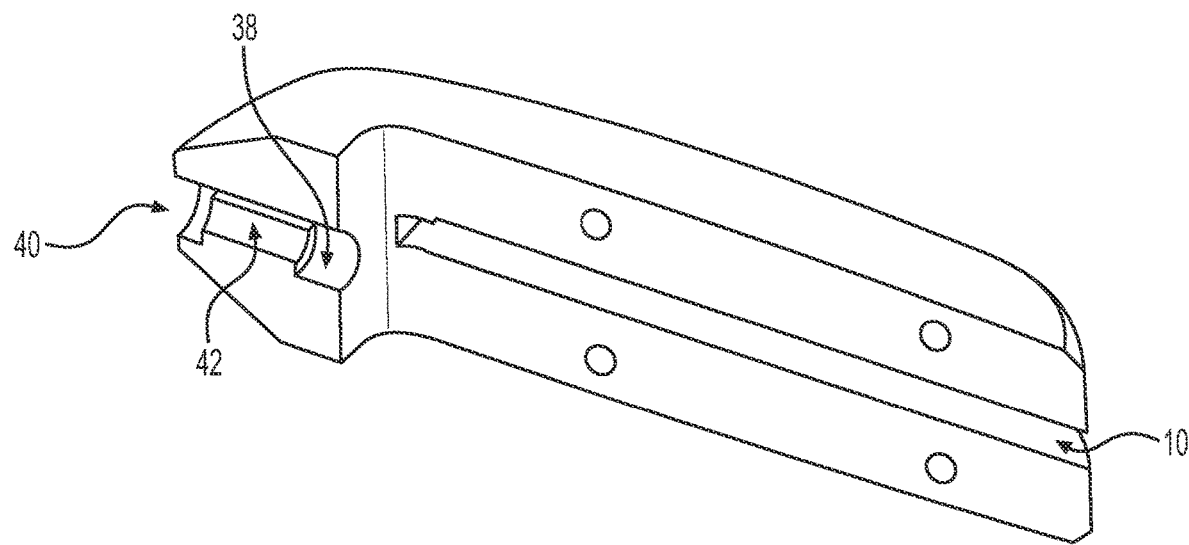
Figure 2E:
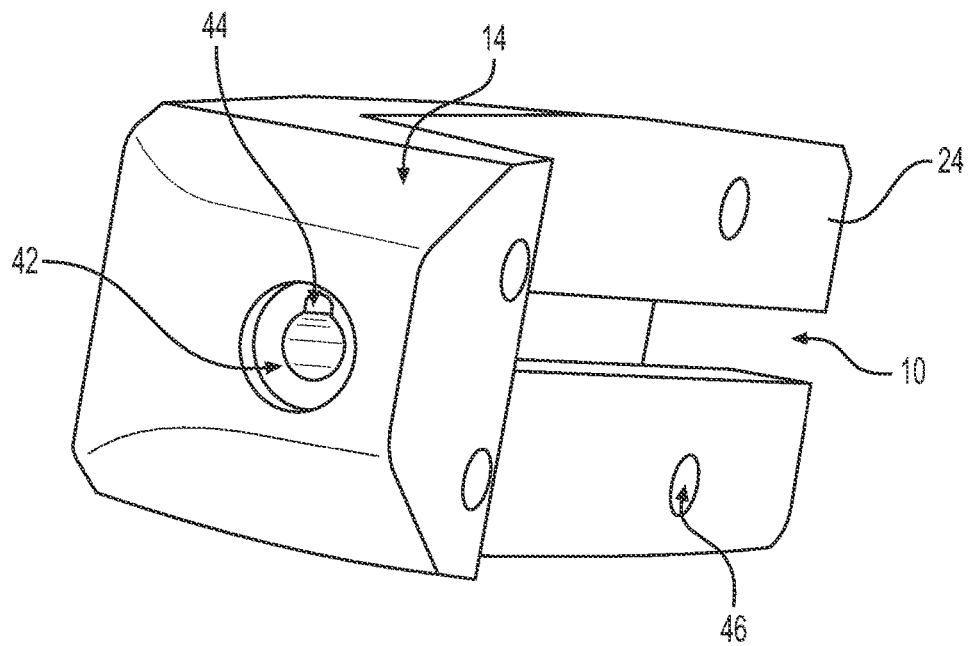
FIG. 2E illustrates a perspective view of one embodiment of a primary base member described herein.

As illustrated in FIG. 2C, the leading end 14 may be tapered. For example, the leading end 14 can include a tapered height (e.g., as measured between the superior surface 20 and the inferior surface 22) and/or a tapered width (e.g., as measured between the inner side surface 24 and the outer side surface 26). In use, the tapered leading end 14 may advantageously be configured to distract tissue during insertion. As illustrated in FIGS. 2A and 2C, the leading end 14 can include a tool-engaging recess 36. The tool-engaging recess 36 can pass longitudinally through the leading end 14, for example, along an axis parallel to the longitudinal axis 12 of the elongate slot 10. As illustrated in FIGS. 2B and 2D, the axis of the tool-engaging recess may be displaced, e.g., posteriorly, relative to the longitudinal axis 12 of the elongate slot 10. As illustrated in FIGS. 2B and 2D, the tool-engaging recess 36 can include an inner opening 38, an outer opening 40, and a narrowed passageway 42 therebetween. In some embodiments, the narrowed passageway 42 can include a non-circular transverse cross-section. For example, as illustrated in FIG. 2E, the narrowed passageway 42 can include an axially-extending notch 44. As described further herein, the notch 44 may advantageously be keyed to engage a driver or other tool. As illustrated in FIG. 2E, the inner side surface 24 can include at least one receptacle 46. The receptacle 46 can be configured to receive at least a portion of the guide member 6 therein and can be, for example, cylindrical. In some embodiments, the primary base member 2 can include a plurality of receptacles configured to engage a plurality of guide members. For example, the primary base member 2 can include 2, 4, 6, 8, 10, or more receptacles. In some embodiments, the primary base member 2 can include at least one pair of vertically-aligned receptacles, wherein a first receptacle is positioned above the elongate slot 10 and a second receptacle is positioned below the elongate slot 10, as illustrated, for example, in FIG. 2E.

Figure 3A:
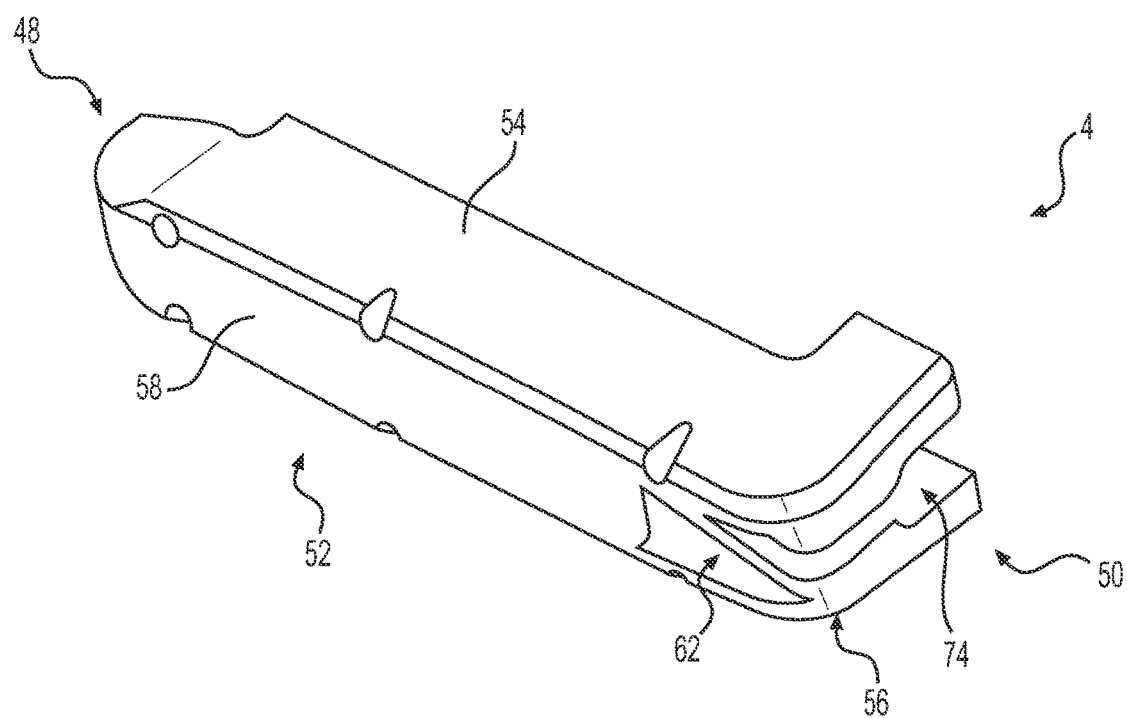
FIG. 3A illustrates a perspective view of one embodiment of a movable base member described herein.

As illustrated in FIG. 3A, the movable base member 4 can include a leading end 48, a trailing end 50, and a side wall 52 therebetween. The movable base member 4 may include a length as measured between the leading end 48 and the trailing end 50. Although not limited to any particular orientation, in some embodiments the movable base member 4 may be configured to be oriented posteriorly in a patient, relative to the primary base member 2, and the side wall 52 may thus be referred to as a posterior side wall. In some embodiments, the movable base member 4 may have a maximum height that is less than a maximum height of the primary base member 2, so as to match the natural lordosis of a spine. In these embodiments, the expandable spinal implant 100 may be wedge-shaped. In other embodiments, the expandable spinal implant 100 may have a constant height. The movable base member 4 can also include a superior surface 54, an inferior surface 56, an outer side surface 58, and, as illustrated in FIG. 3D, an inner side surface 60. In some embodiments, the outer side surface 58 may include a section that is straight or generally straight (e.g., non-curved), as viewed from the superior and/or inferior surfaces 54, 56. The superior and inferior surfaces 54, 56 may be convex, as viewed from the outer side surface 58, leading end 48, and/or trailing end 50. As described herein, the superior and/or inferior surfaces 54, 56 may include a plurality of texturizing members.

Figure 3B:
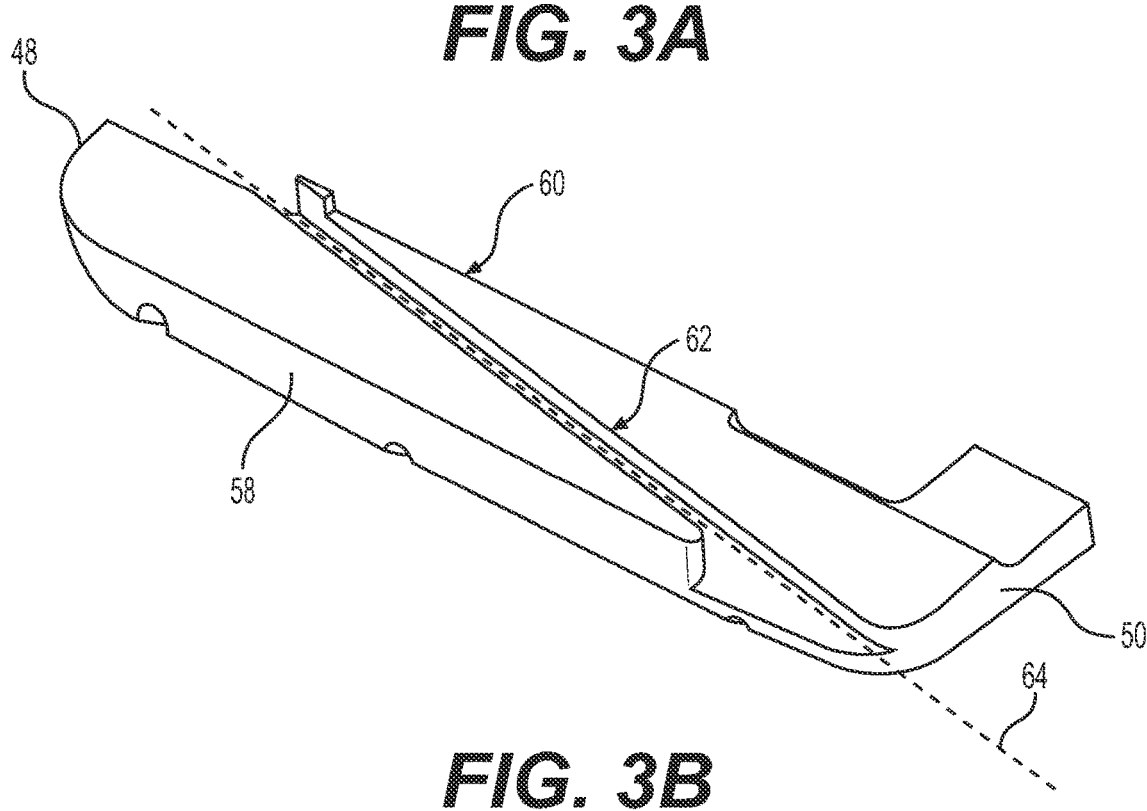
FIGS. 3B-C illustrate cross-sectional views of one embodiment of a movable base member described herein.
Figure 3C:
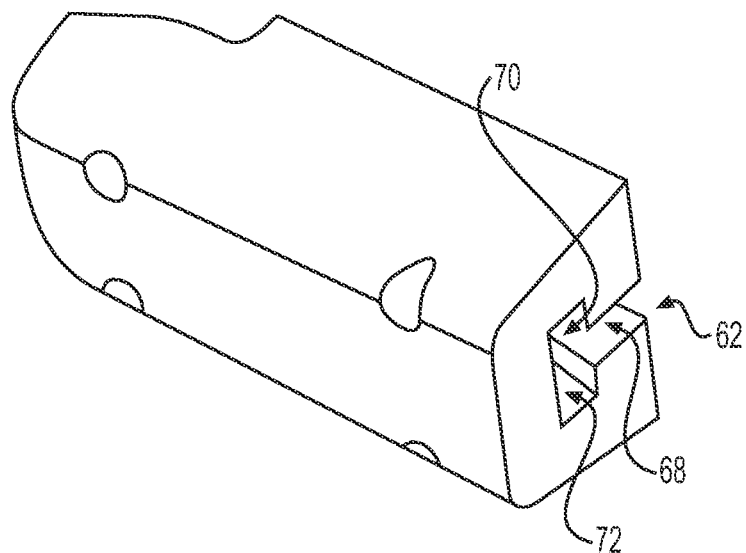
Figure 3D:
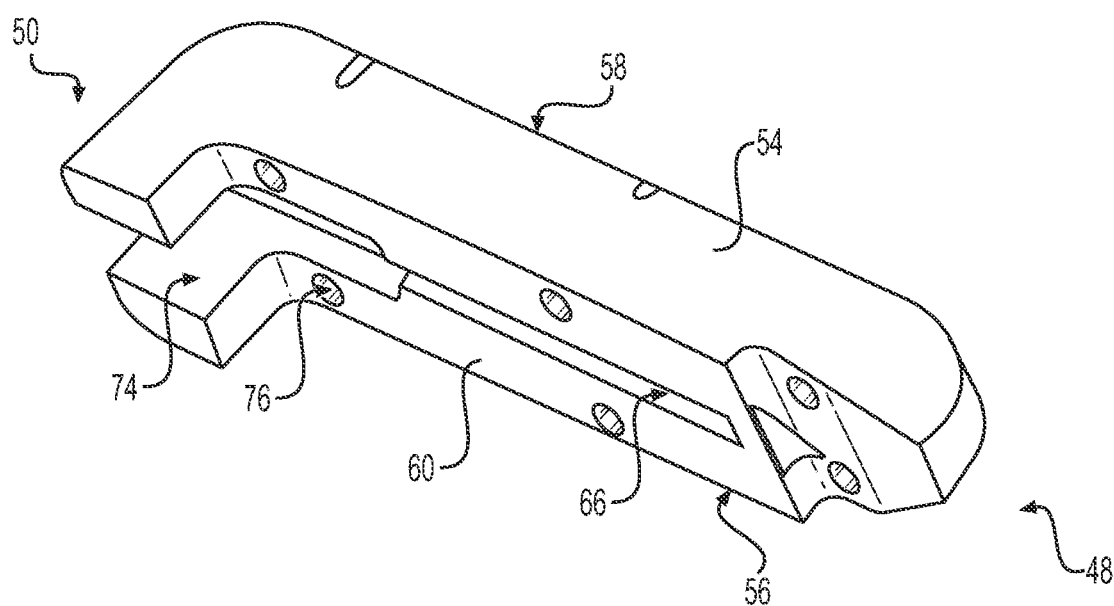
FIG. 3D illustrates a perspective view of one embodiment of a movable base member described herein.

The movable base member 4 can include an elongate slot 62, as illustrated in FIGS. 3A-B. The elongate slot 62 may extend at least partially along the length of the movable base member 4 and may intersect at least one side surface thereof. The elongate slot 62 can include a longitudinal axis 64, which may intersect the inner and/or outer side surfaces 58, 60. As illustrated in FIG. 3B, the longitudinal axis 64 may intersect the outer side surface 58 at the trailing end 50 and/or may intersect the inner side surface 60 at the leading end 48. Accordingly, the longitudinal axis 64 of the elongate slot 62 may be angled relative to (e.g., may intersect) a longitudinal axis 64 of the movable base member 4, as illustrated in FIG. 3B. Furthermore, in some embodiments, the elongate slot 62 may be referred to as an angled slot. As illustrated in FIG. 3D, the elongate slot 62 can include an opening 66 that extends along the inner side surface 60 of the movable base member 4. The opening 66 may also extend at least partially along the trailing end 50, as illustrated in FIG. 3D. As illustrated in FIG. 3C, the elongate slot 62 can include a main passageway 68 and a supplemental passageway, the supplemental passageway including first and second corridors 70, 72. The first and second corridors 70, 72 may each extend in opposite directions at a 90 degree angle away from the main passageway 69. Accordingly, the elongate slot 62 can include a T-shaped transverse cross-section.

As illustrated in FIG. 3D, the leading end 48 may be tapered. For example, the leading end 48 can include a tapered height (e.g., as measured between the superior surface 54 and the inferior surface 56) and/or a tapered width (e.g., as measured between the inner side surface 60 and the outer side surface 58). In use, the tapered leading end 48, alone or in conjunction with the leading end 14 of the primary base member 2, may be used to distract tissue during insertion. As illustrated in FIG. 3A, the trailing end 50 can include a channel 74 passing longitudinally therethrough. The channel 74 may be configured to receive a tool, such as a driver, therethrough. In some embodiments, the channel 74 may include a rounded or curved inner surface; in other embodiments, it may include an angled inner surface. In some embodiments, the channel 74 may include a threaded interior. The channel 74 may not be fully enclosed and may be U-shaped. In some embodiments, the channel 74 may have an opening that extends at least partially along the inner side surface 60. In an assembled and collapsed or closed configuration, the channel 74 of the trailing end 50 of the movable base member 4 may be configured to be coaxial with the tool-engaging recess 36 of the leading end 14 of the primary base member 2. As illustrated in FIG. 3D, the inner side surface 60 can include at least one receptacle 76. The receptacle 76 can be configured to receive at least a portion of the guide member 6 therein, and can be, for example, cylindrical. In some embodiments, the movable base member 4 can include a plurality of receptacles configured to engage a plurality of guide members. For example, the movable base member 4 can include 2, 4, 6, 8, 10, or more receptacles. In some embodiments, the movable base member 4 can include at least one pair of vertically-aligned receptacles, wherein a first receptacle is positioned above the elongate slot 62 and a second receptacle is positioned below the elongate slot 62, as illustrated in FIG. 3D.

As illustrated in FIG. 1, the guide member 6 may be a cylindrical pin. The guide member 6 can include a first end 78 configured to be coupled with the primary base member 2 and a second end 80 configured to be coupled with the movable base member 4. The guide member 6 may be configured to be reversibly or irreversibly coupled with the primary and/or movable base members 2, 4. In some embodiments, the guide member 6 may be integral to the primary and/or movable base members 2, 4. The guide member 6 may be configured to be received within any of the receptacles (e.g., receptacle 46 and/or 76) of the primary and/or movable base members 2, 4. The guide member 6 may be configured to be simultaneously received within the primary and movable base members 2, 4 when the expandable spinal implant 100 is assembled (in an expanded and/or contracted configuration). The guide member 6 may thus include a length, as measured between the first and second ends 78, 80, which is not greater than a width of the expandable spinal implant 100, as measured from the outer side surface 26 to the outer side surface 58. Additionally, the guide member 6 may include a diameter that is not greater than a diameter of the receptacles 46 and/or 76. Furthermore, the guide member 6 may be configured to translate within the receptacles 46 and/or 76. As illustrated in FIG. 1, the expandable spinal implant 100 may include a plurality of guide members 6, such as at least one pair thereof. For example, the expandable spinal implant 100 can include 2, 4, 6, 8, 10, or more guide members 6.

As illustrated in FIG. 1, the actuator 8 can include a first arm 82 and a second arm 84, each extending from a central member 98. The first and second arms 82, 84 may extend in opposite directions. The first arm 82 can be configured to slideably engage and/or be received within the elongate slot 10 and the second arm 84 can be configured to slideably engage and/or be received within the elongate (e.g., angled) slot 62. Those skilled in the art may appreciate that each of the first and second arms 82, 84 can include a T-shaped end configured to be received within the T-shaped elongate slots 10, 62. The first arm 82 can include a first projection 86, the first projection 86 including an upper prong 90 and a lower prong 92, wherein each of the upper and lower prongs 90, 92 extend in opposite directions at a 90 degree angle from the first arm 82. The upper and lower prongs 90, 92 may be coaxial. The first arm 82 and first projection 86 may be coplanar. The second arm 84 can include a second projection 88, the second projection 88 including an upper prong 94 and a lower prong 96, wherein each of the upper and lower prongs 94, 96 extend in opposite directions at a 90 degree angle away from the second arm 84. The upper and lower prongs 94, 96 may be coaxial. The second arm 84 and the second projection 88 may be coplanar. The first and/or second projections 86, 88 may each have a height that is not greater than a height of the supplemental passageways of the primary and movable base members 2, 4, respectively. The actuator 8 may have a width (e.g., as measured from the first projection 86 to the second projection 88) that is not greater than a width of the expandable implant 100. The central member 98 can include a threaded hole 102 extending therethrough. The threaded hole 102 may include an axis that is perpendicular to an axis of the first arm 82, second arm 84, first projection 86, and/or second projection 88. When in an assembled configuration (e.g., when the first and second projections 86, 88 are slideably received within the elongate and angled slots 10, 62), either expanded or collapsed, the threaded hole 102 may be configured to be coaxial with the tool-engaging recess 36 of the primary base member 2. In some embodiments, the central member 98 may include a generally cylindrical or rounded exterior. The central member 98 may be configured to be received and/or nested within the channel 74 of the movable base member 4. The central member 98 may have an outer dimension (e.g., height, width, and/or diameter) that is less than that of the channel 74.

When the expandable spinal implant 100 is assembled, for example, as illustrated in FIGS. 4A-F, the primary and movable base members 2, 4 may be oriented or positioned next to each other with the leading ends 14, 48 at one end (e.g., at the leading end 3 of the implant 100), the trailing ends 16, 50 at another end (e.g., at the trailing end 5 of the implant 100), and the inner side surfaces 24, 60 facing each other. Expandable window 104 may be defined between the primary and movable base members 2, 4. In use, the expandable window 104 may be configured to receive a biomaterial such as bone graft material, demineralized bone matrix, bone chips, and/or bone morphogenetic proteins. Those skilled in the art may appreciate that, in an assembled configuration, the distance between the elongate slot 10 and the angled slot 62 may decrease towards the leading ends 14, 48. Additionally, the actuator 8 may be disposed and/or located between the primary and movable base members, 2, 4, with the first projection 86 of the actuator slideably disposed within the elongate slot 10 and the second projection 88 of the actuator 8 slideably disposed within angled slot 62. At least a portion of the first end 78 of the guide member 6 may be slideably disposed or located within the receptacle 46 of the primary base member 2 and at least a portion of the second end 80 may be slideably disposed or located within the receptacle 76 of the movable base member 4.

Figure 4A:
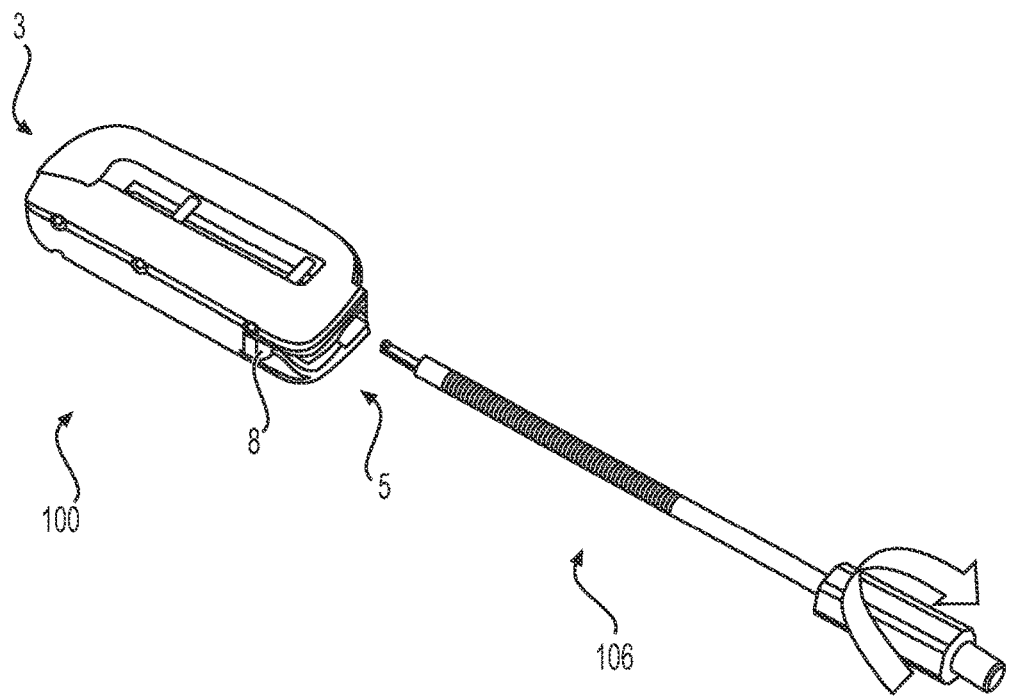
FIG. 4A illustrates a perspective view of one embodiment of an expandable spinal implant and a driver as described herein.
Figure 4B:
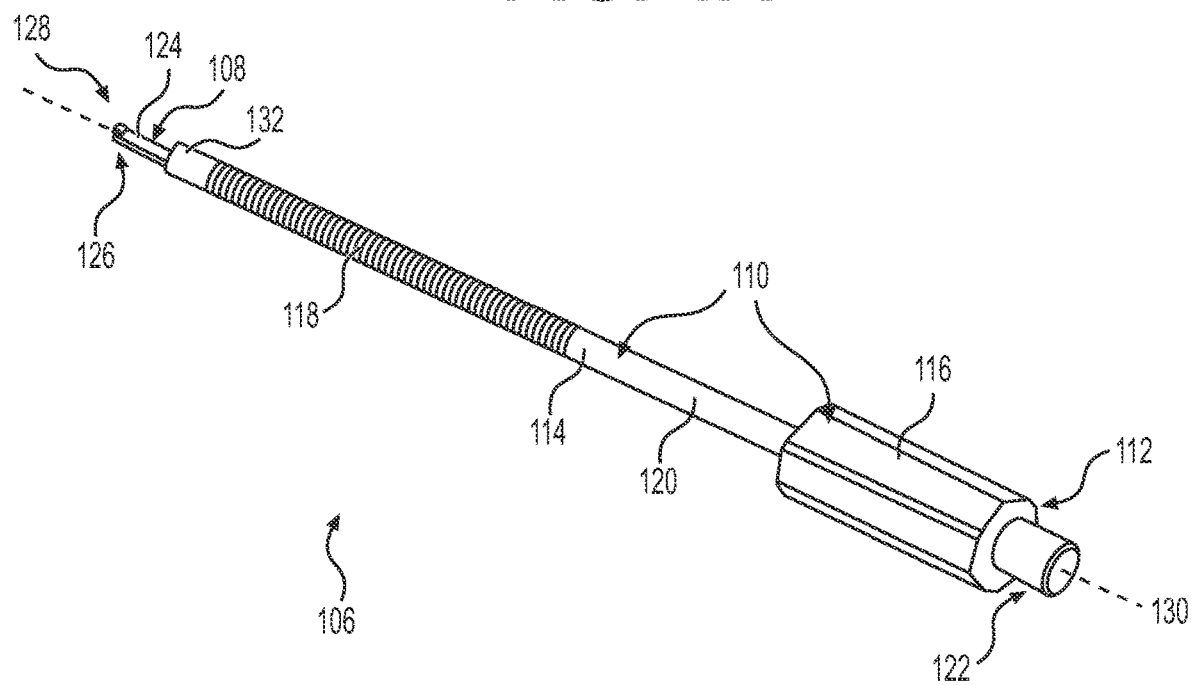
FIG. 4B illustrates a perspective view of one embodiment of a driver described herein.
Figure 4C:
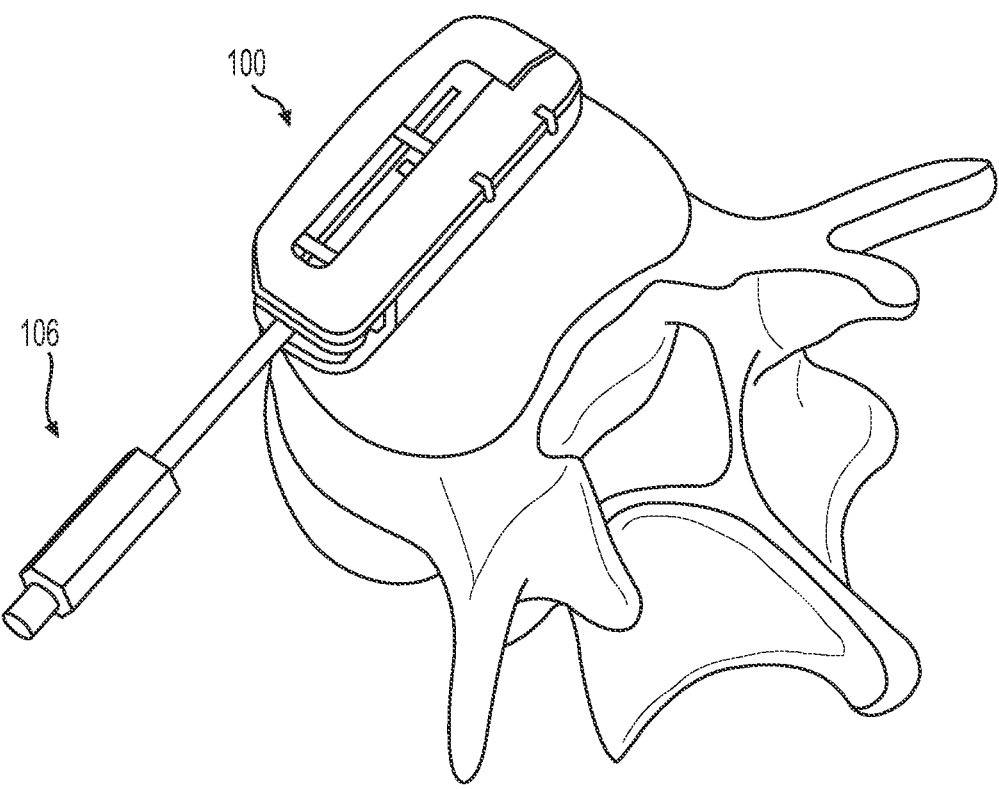
FIGS. 4C-E illustrate perspective views of one embodiment of an expandable spinal implant and a driver as described herein.
Figure 4D:
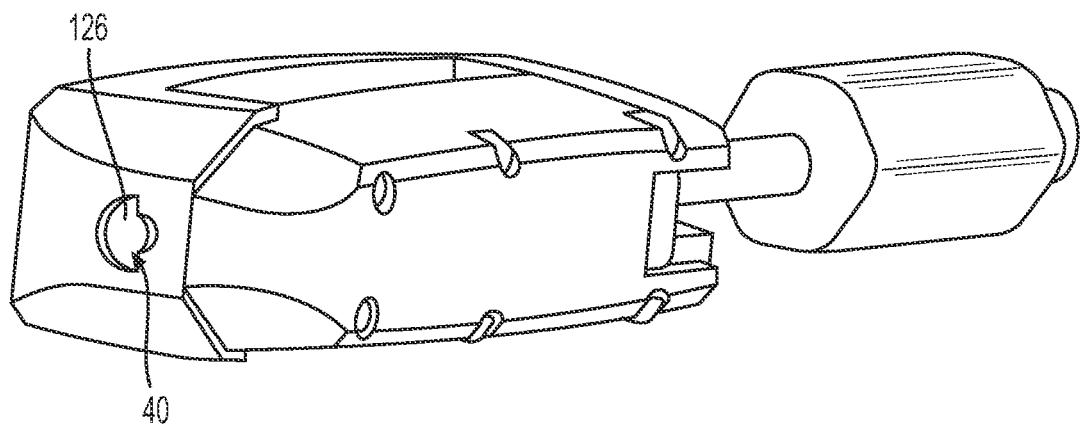
Figure 4E:
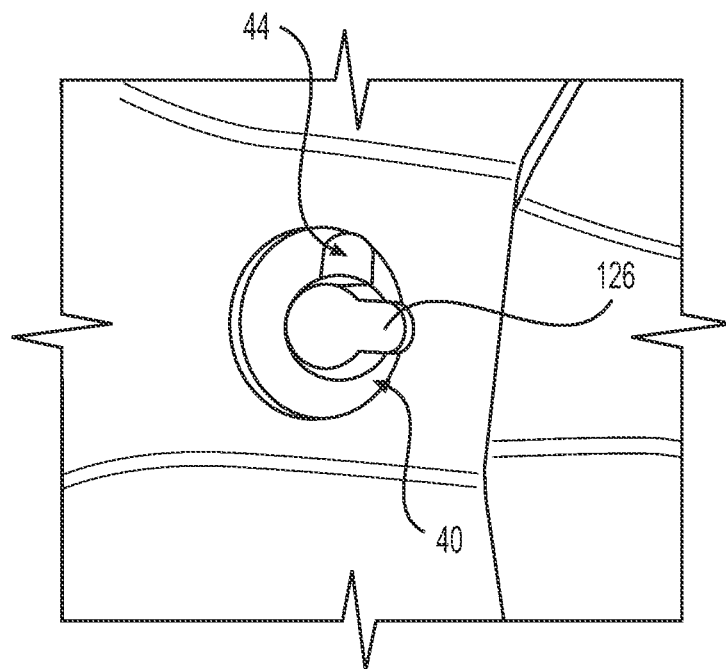
Figure 4F:
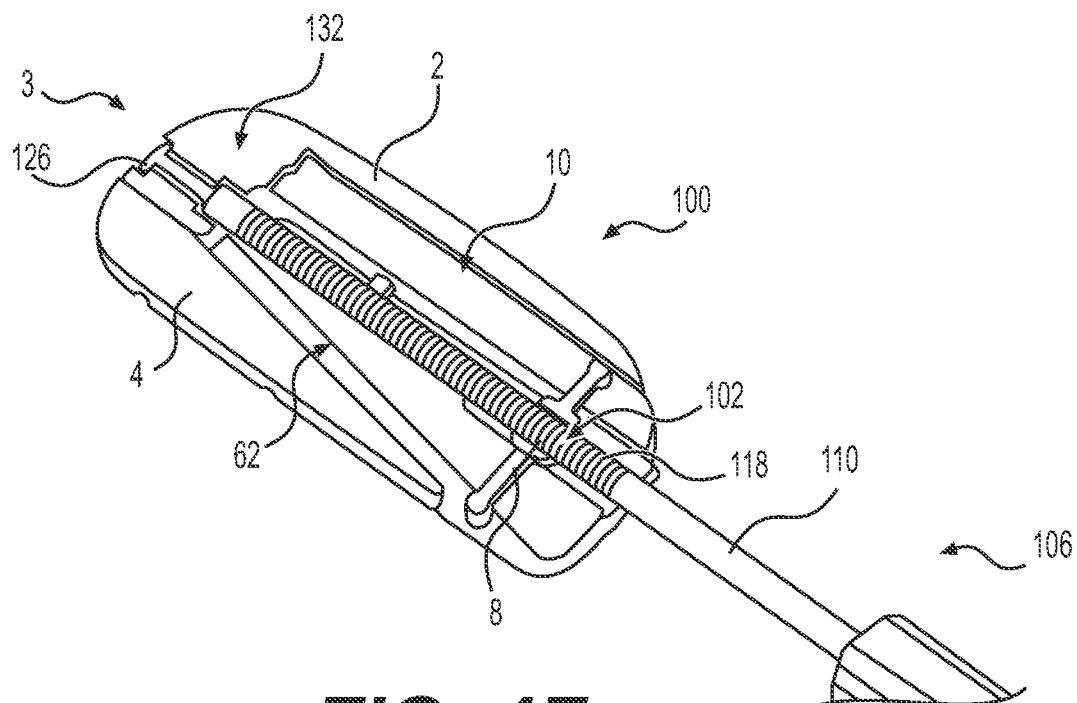
FIGS. 4F-G illustrate cross sectional views of one embodiment of an expandable spinal implant and a driver as described herein.
Figure 4G:
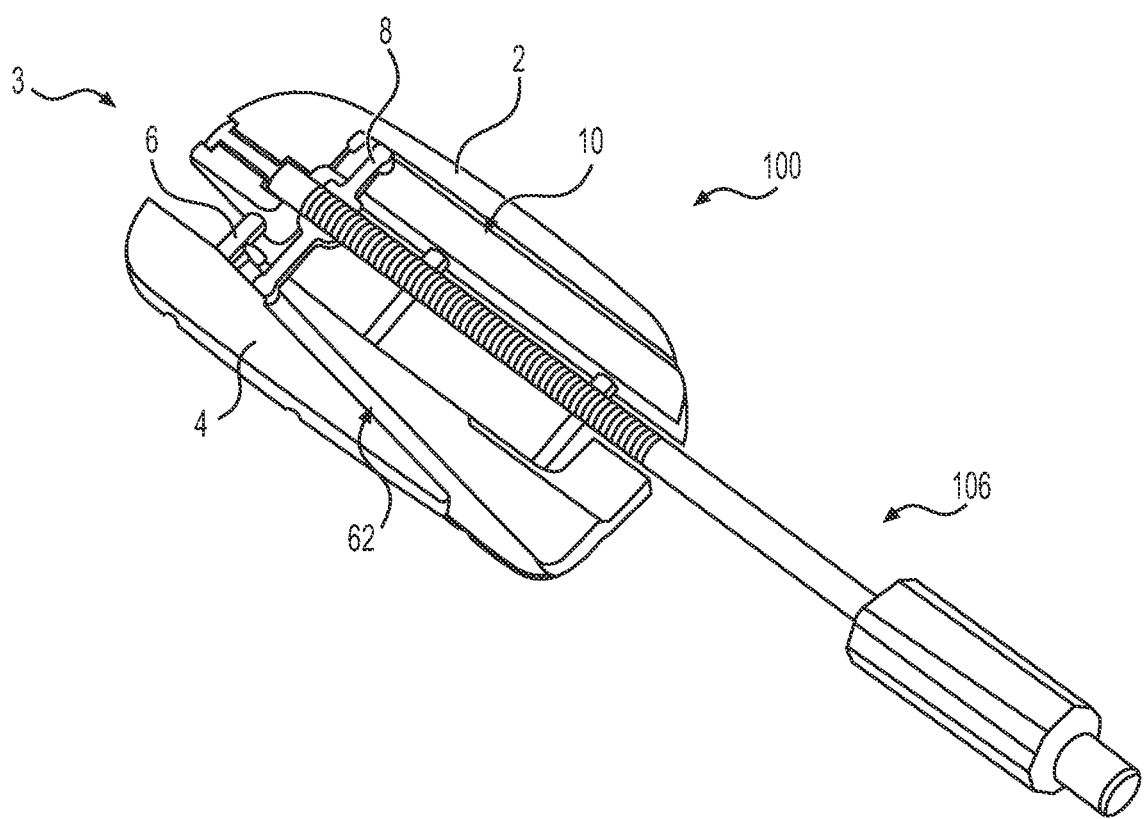

As described herein, when assembled, the expandable spinal implant 100 may be configured to reversibly transition between an expanded configuration and a collapsed configuration, wherein the width of the implant 100 is greater in the expanded configuration than in the collapsed configuration. In the collapsed configuration, for example, as illustrated in FIG. 4A, the actuator 8 may be disposed and/or located at the trailing end 5 of the implant 100. In use, the expandable spinal implant 100 may expand (e.g., may transition from the collapsed configuration to the expanded configuration) by actuating, driving, pushing, pulling, sliding, translating, and/or moving the actuator 8 laterally along the elongate and angled slots 10, 62 towards the leading end 3 of the implant 100, as illustrated in FIGS. 4F-G. Those skilled in the art may appreciate that because the distance between the elongate slot 10 and the angled slot 62 narrows, the second arm 84 of the actuator 8 may push the movable base member 4 outwards (e.g., posteriorly and/or away from the primary base member 2) as it travels towards the leading end 3, thereby expanding the implant 100. The guide member(s) 6 may assist, encourage, facilitate, and/or promote linear motion of the movable base member 4 away from the primary base member 2.

As illustrated in FIG. 4A, in some embodiments, a driver 106 may be used to actuate, push, pull, slide, translate, and/or move the actuator 8 to thereby expand and/or collapse the implant 100. As illustrated in FIG. 4B, the driver 106 may include an inner shaft 108 disposed within an outer shaft 110. The inner and outer shafts 108, 110 may be coaxial (e.g., may share a common longitudinal axis, such as longitudinal axis 130). The outer shaft 110 and the inner shaft 108 may be configured to rotate relative to (e.g., independently of) each other. The outer shaft 110 can include an elongate rod portion 114 extending from a handle portion 116. The outer shaft 110 may also include a distal tip 132 at a distal-most end of the elongate rod portion 114. The elongate rod portion 114 can include a distal threaded section 118, which may be configured to engage the threaded hole 102 of the actuator 8. The elongate rod portion 114 may also include a proximal non-threaded section 120. The elongate rod portion 114 may a constant outer diameter. In some embodiments, the elongate rod portion 114 may be configured to nest and/or be received within the channel 74 of the movable base member 4. Accordingly, in some embodiments, the elongate rod portion 114 or a section thereof (e.g., non-threaded section 120) may include an outer diameter that is less than a height of the channel 74. The handle 116 may include a gripping surface, and may, for example, include a rounded or angled exterior. The handle 116 may be configured to be grasped by a user.

As illustrated in FIG. 4A, the outer shaft 110 can include a cylindrical cannula 112 extending along a longitudinal axis therethrough. The inner shaft 108 may be located within the cylindrical cannula 112. The inner shaft 108 may be configured to rotate within the cannula 112. The inner shaft 108 can include a proximal knob 122 that is configured to extend proximally from the outer shaft 110. The proximal knob 122 may include a gripping surface and/or may be configured to be grasped by a user. The inner shaft 108 can also include an elongate rod portion 124 extending from the knob 122. The inner shaft 108 can also include a key member 126 at a distal end 128 of the elongate rod portion 124. The key member 126 can include a protrusion that extends at an angle away from the longitudinal axis 130. For example, the key member 126 may extend perpendicularly to the longitudinal axis 130. In other embodiments, the key member 126 can include a hook or a bend at the distal end 128 of the elongate rod portion 124. The key member 126 may be keyed to fit within the notch 44 of the primary base member 2. Accordingly, at least a portion of the distal end 128, including key member 126, may be sized and/or configured to fit within and/or pass through the tool-engaging recess 36 of the primary base member 2. In some embodiments, the driver 106 may also include one or more locking members to prevent or inhibit translational motion of the inner and/or outer shafts 108, 110 relative to each other. The driver 106 may also include one or more seals, washers, and/or o-rings between the inner and outer shafts 108, 110.

Embodiments herein are also directed to methods of installing the expandable spinal implant 100. These methods can include providing the implant 100 in the closed or collapsed configuration as described herein, where the implant 100 has a closed or collapsed width. These methods can also include expanding the implant 100 to an expanded width by translating the actuator 8 from the trailing end 5 of the implant 100 towards the leading end 3 of the implant 100 to thereby separate (e.g., increase the distance between) the movable base member 4 from the primary base member 2.

In some embodiments, the step of providing the expandable spinal implant 100 in the closed or collapsed configuration can include inserting the implant 100 into a selected location, such as a cavity between two vertebral bodies created by a discectomy or other procedure. The implant 100 can be inserted into the cavity using a variety of approaches, such as anteriorly, posteriorly, transforaminally, or laterally. In some embodiments, the implant 100 may advantageously be configured to be inserted into an intervertebral space using a lateral procedure. Those skilled in the art may appreciate that, in some embodiments, when in the closed or collapsed configuration, the expandable spinal implant 100 may have a width that is about 10-30% less than the width in the expanded configuration. In some embodiments, the closed or collapsed width of the implant 100 may be about 15-25% less than the expanded width. Advantageously, the implant 100 may be inserted through a smaller, less-invasive opening that may result in reduced trauma to muscles, nerves, or other tissue. When used in a lateral procedure (e.g., lateral lumbar interbody fusion), the implant 100 may be inserted laterally in the far anterior side of the intervertebral space, for example, as illustrated in FIG. 4C. This technique can advantageously reduce or minimize interaction with the posteriorly-located lumbar plexus.

In some embodiments, the driver 106 can be used to translate the actuator 8 from the trailing end to the leading end of the implant 100. This step can include inserting the driver 106 into the implant 100 through the trailing end thereof, as illustrated in FIGS. 4C-D. This step can also include coupling the distal threaded section 118 of the driver 106 with the threaded hole 102 of the actuator 8. For example, the distal threaded section 118 can be threaded into the threaded hole 102. In some embodiments, the threading may be accomplished by applying a rotational force to the handle 116 while engaging the knob 122 to prevent or inhibit rotation of the inner shaft 108. This step can also include inserting at least a portion of the distal end 128 into the tool-engaging recess 36, as illustrated in FIG. 4D, until the key member 126 is seated within the outer opening 40 of the tool-engaging recess 36 and the distal tip 132 is seated within the inner opening 38 and abuts the narrowed passageway 42.

The driver 106 can then be locked, anchored, and/or secured within the implant 100. As illustrated in FIGS. 4D-E, this step can include rotating the inner shaft 108 by an angle greater than 0 degrees and less than 360 degrees (e.g., by an angle between 90 degrees and 270 degrees) until the key member 126 is out of alignment with the notch 44. This step may be accomplished by applying a rotational force to the knob 122 while engaging the handle 116 to prevent or inhibit rotation of the outer shaft 110. As illustrated in FIG. 4F, those skilled in the art may appreciate that, when locked, the key member 126 and/or the distal tip 132 may prevent or inhibit translational movement of the driver 106 relative to the implant 100.

The outer shaft 110 can then be rotated. The distal threaded section 118 can engage the threaded hole 102 of the actuator 8 to actuate, drive, push, pull, slide, translate, and/or move the actuator 8 laterally along the elongate and angled slots 10, 62 towards the leading end 3 of the implant 100, thereby separating the movable base member 4 from the primary base member 2, as illustrated in FIGS. 4F-G.

Those skilled in the art may appreciate that, in some embodiments, the expandable spinal implant 100 may be configured to expand to a greater width, effectively providing benefits of a larger implant, without utilizing a larger incision. For example, in some embodiments, when in the expanded configuration, the expandable spinal implant 100 may have a width that is about 15-40% greater than the width in the collapsed or closed configuration. In some embodiments, the expanded width of the implant 100 may be about 20-35% greater than the expanded width. Advantageously, the expandable spinal implant 100 may be configured to more evenly distribute the vertebral load, increase surface area contact with the vertebral endplates, engage bone adjacent the apophyseal ring, reduce or inhibit cage subsidence, and/or promote increased fusion by being configured to receive more biomaterials, without increasing trauma to the patient.

Some methods can also include disengaging the driver 106 from the implant 100. This step can include rotating the inner shaft 108 until the key member 126 is aligned with the notch 44. This step can also include rotating the outer shaft 110 to unthread the distal threaded section 118 from the actuator 8. The step can also include removing the driver 106 from the implant 100. Optionally, a biomaterial may then be inserted into the expandable window 104 through the channel 74.

Some methods herein are directed to collapsing the implant 100. These methods can include providing the implant 100 in the expanded configuration, as described herein, and collapsing the implant 100 by translating the actuator 8 from the leading end 3 of the implant 100 to the trailing end 5 of the implant 100 to thereby bring together (e.g., reduce the distance between) the movable base member 4 and the primary base member 2. In some embodiments, the driver 106 can be used to translate the actuator 8 from the leading end 3 to the trailing end 5. Those skilled in the art may appreciate that the same general steps involved with expansion of the implant 100 may apply, except that the outer shaft 110 may be rotated in the opposite direction to translate the actuator 8 towards the trailing end 5.

Figure 5A:
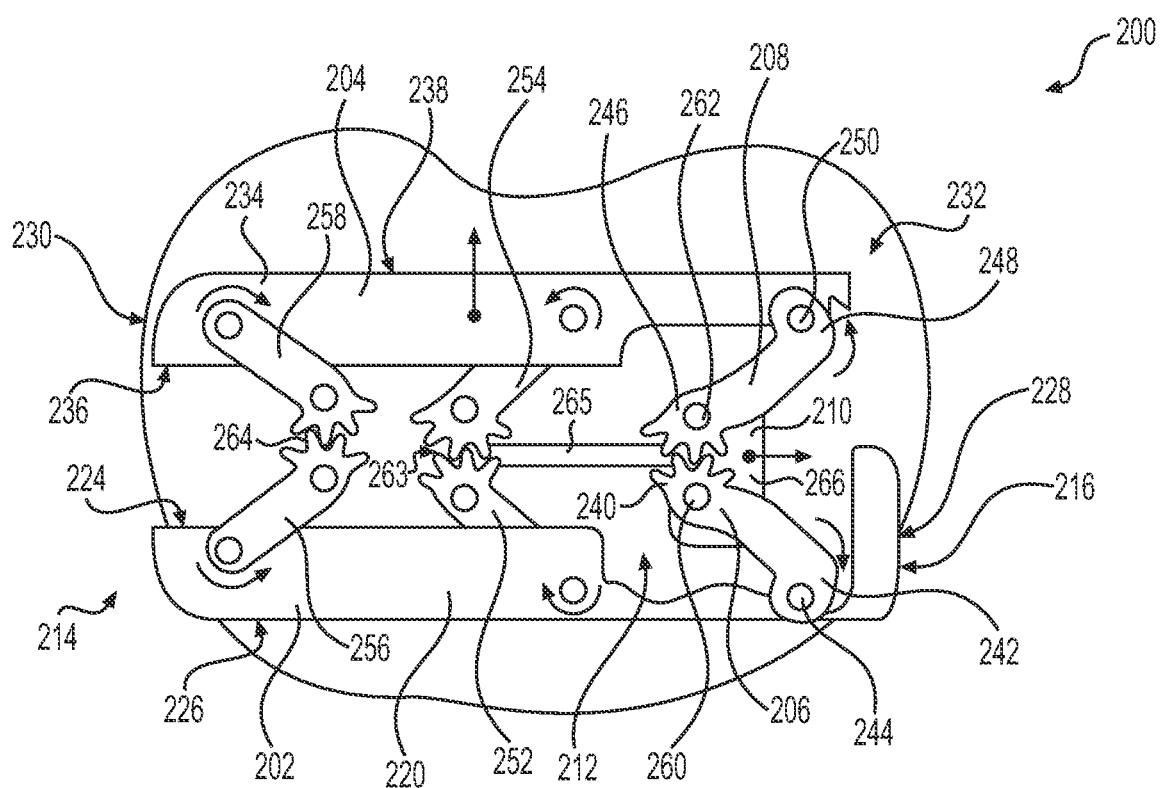
FIGS. 5A-B illustrate perspective views of one embodiment of an expandable spinal implant described herein.
Figure 5B:
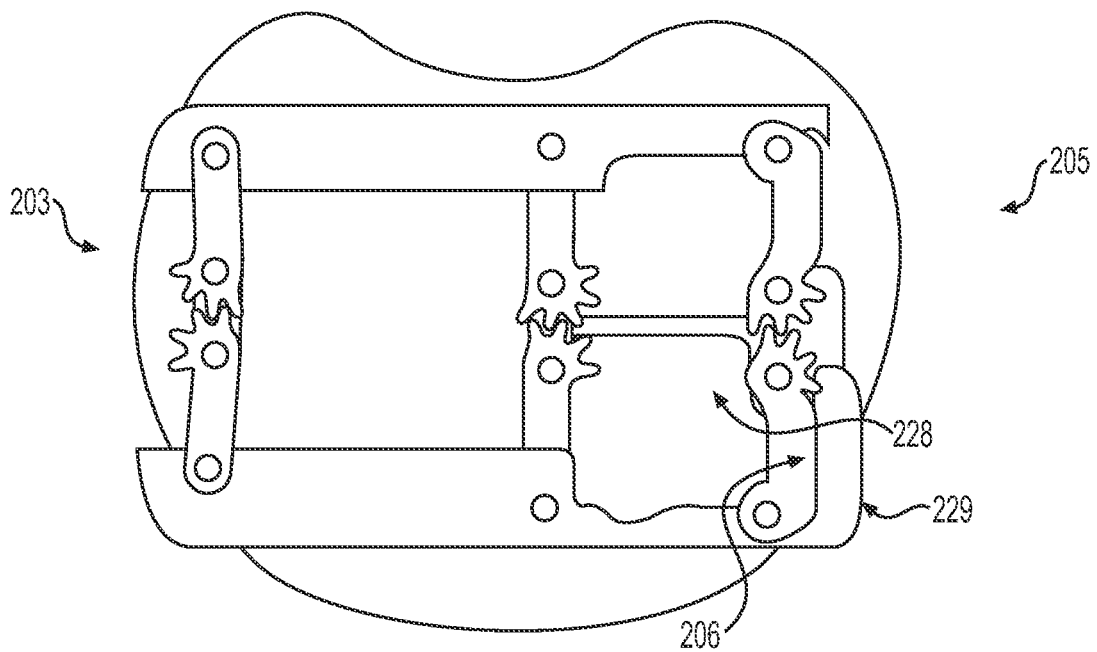

Turning now to FIGS. 5A-B, some embodiments herein are directed to an expandable spinal implant 200 that can include a first (e.g., anterior) elongate body 202, a second (e.g., posterior) elongate body 204, a first (e.g., anterior) arm 206, a second (e.g., posterior) arm 208, and a connector member (e.g., connector member 210). The implant 200 may include a leading end 203 and a trailing end 205, as illustrated in FIG. 5B. As described further herein, the first and/or second elongate bodies 202, 204 may be configured to move (e.g., translate) relative to each other. The expandable spinal implant 200 may advantageously be configured to transition between an expanded configuration and a collapsed or closed configuration, wherein the implant 200 has a width, as measured between an outer side surface of the first elongate body 202 and an outer side surface of the second elongate body 204, that is greater in the expanded configuration than in the collapsed configuration. In some embodiments, the implant 200 may have a collapsed width in the range of from about 10 mm to about 15 mm, and an expanded width in the range of from about 25 mm to about 30 mm. The first and second elongate bodies 202, 204 may define an expandable window 212 therebetween. The expandable window 212 may be configured to receive a fusion-enhancing material or other biomaterial, as described herein.

As illustrated in FIG. 5A, the first elongate body 202 can include a leading end 214 and a trailing end 216. The first elongate body 202 may have a length as measured between the leading end 214 and the trailing end 216. Although not limited to any particular orientation, in some embodiments the first elongate body 202 may be configured for anterior orientation in a patient and may thus be referred to as an anterior elongate body. The first elongate body 202 can also include a superior surface 220, an inferior surface opposite the superior surface 220 (not shown), an inner side surface 224, and an outer side surface 226. In some embodiments, at least a portion of the inner side surface 224 may include an elongate slot or groove (not shown) extending longitudinally thereon. The first elongate body 202 may have a width as measured between the inner side surface 224 and the outer side surface 226. In some embodiments, the outer side surface 226 may be convex, as viewed from the superior and/or inferior surfaces. The superior surface 220 and/or inferior surface may be convex, as viewed from the outer side surface 226, leading end 214, and/or trailing end 216. In other embodiments, the superior surface 220 and/or inferior surface may be angled and/or slanted, such that the height of the first elongate body 202 is greater at the outer side surface 226 than at the inner side surface 224. As described herein, the superior and/or inferior surfaces may include a plurality of texturizing members.

As illustrated in FIGS. 5A-B, the leading end 214 of the first elongate body 202 may be tapered. For example, the leading end 214 can include a tapered height (e.g., as measured between the superior surface 220 and the inferior surface) and/or a tapered width (e.g., as measured between the inner side surface 224 and the outer side surface 226). In use, the tapered leading end 214 may advantageously be configured to distract tissue during insertion.

As illustrated in FIGS. 5A-B, the trailing end 216 of the first elongate body 202 may be wider than the leading end 214. In some embodiments, the width of the trailing end 216 may be equal to the width of the implant 200 in the collapsed configuration. The trailing end 216 can include a channel 228 extending therethrough. The channel 228 may include an axis that is parallel to the length of the first elongate body 202. In some embodiments, the axis may be configured to intersect the connector member 210. The channel 228 may be configured to receive a tool, such as a driver, therethrough. In some embodiments, the channel 228 may include a rounded or curved inner surface; in other embodiments, it may include an angled inner surface. In some embodiments, the channel 228 may include a threaded interior. The channel 228 may not be fully enclosed and may be U-shaped. In some embodiments, the channel 228 may have an opening that extends at least partially along the inner side surface 224. The trailing end 216 may also include a threaded hole 229 that extends entirely therethrough, as illustrated in FIG. 5B. For example, the threaded hole 229 may be in fluid communication with the expandable window 212. The threaded hole 229 may extend along an axis that is parallel to the length of the first elongate body 202. The threaded hole 229 may be configured to threadably receive a set screw therein. In some embodiments, the trailing end 216 and/or other section of the first elongate body 202 can include a channel configured to receive bone growth material therethrough.

As illustrated in FIG. 5A, the second elongate body 204 can include a leading end 230 and a trailing end 232. The second elongate body 204 may have a length as measured between the leading end 230 and the trailing end 232. The length of the second elongate body 204 may be generally equal to the length of the first elongate body 202. Although not limited to any particular orientation, in some embodiments the second elongate body 204 may be configured for posterior orientation in a patient and may thus be referred to as a posterior elongate body. The second elongate body 204 can also include a superior surface 234, an inferior surface opposite the superior surface 234 (not shown), an inner side surface 236, and an outer side surface 238. In some embodiments, at least a portion of the inner side surface 236 may include an elongate slot or groove (not shown) extending longitudinally thereon. The second elongate body 204 may have a width as measured between the inner side surface 236 and the outer side surface 238. In some embodiments, at least a portion of the outer side surface 238 may be straight or generally straight (e.g., non-curved), as viewed from the superior and/or inferior surfaces. The superior surface 234 and/or inferior surface may be convex, as viewed from the outer side surface 238, leading end 230, and/or trailing end 232. In other embodiments, the superior surface 234 and/or inferior surface may be angled and/or slanted, such that the height of the second elongate body 204 is less at the outer side surface 238 than at the inner side surface 236. In some embodiments, the second elongate body 204 may have a maximum height that is less than a maximum height of the first elongate body 202, so as to match the natural lordosis of a spine. In these embodiments, the expandable spinal implant 200 may be wedge-shaped. In other embodiments, the expandable spinal implant 200 may have a constant height. As described herein, the superior and/or inferior surfaces may include a plurality of texturizing members.

The first arm 206 can include a proximal end 240 and a distal end 242. The proximal end 240 may extend into the expandable window 212. The proximal end 240 can be configured to pivotably and/or hingedly engage the second arm 208. For example, as illustrated in FIG. 5A, the proximal end 240 can include a gear member having teeth configured to mesh with gear teeth on the second arm 208. In other embodiments, the proximal ends of the first and/or second arms 206, 208 may include some other hinged connection member. The distal end 242 may be pivotably coupled to the first elongate body 202. For example, the first arm 206 may be configured to pivot about a pin 244 that is coupled to both the first arm 206 and the first elongate body 202. Accordingly, the first arm 206 may be configured to pivot between a first angle, generally parallel to the first elongate body 202, and a second angle, generally perpendicular to the first elongate body 202. The first arm 206 may be configured to pivot in a plane (e.g., a horizontal plane) that is parallel to a plane defined by both the first and second elongate bodies 202, 204. The first arm 206 may be configured to pivot about an axis that is perpendicular to the length of the first elongate body 202. In some embodiments, the first arm 206 may be coupled to the superior surface 220 of the first elongate body 202. In other embodiments, the first arm 206 may be coupled to the inner side surface 224 and/or disposed within the elongate slot or groove (not shown). In yet other embodiments, the first arm 206 may be coupled to the inferior surface (not shown) of the first elongate body 202.

The first arm 206 may be coupled to the first elongate body 202 anywhere along the length thereof. As illustrated in FIG. 5A, the first arm 206 may be located at the trailing end 216 of the first elongate body 202. In these embodiments, the first arm 206 may be configured to abut the trailing end 216 of the first elongate body 202 when the implant 200 is in the expanded configuration. In some embodiments, the trailing end 216 may prevent or inhibit the first arm 206 from pivoting beyond the length of the implant 200.

In some embodiments, the first arm 206 can extend in a straight or generally straight line between the proximal and distal ends 240, 242. In other embodiments, the first arm 206 can include one or more bends, kinks, curves, and/or angles, for example, as illustrated in FIG. 5A. In some embodiments, a portion of the first arm 206 (e.g., the distal end 242) may be bent at an angle in the range of from about 1 degree to about 90 degrees relative to the rest of the first arm 206.

The second arm 208 can include some or all of the same features as the first arm 206. For example, the second arm 208 can include a proximal end 246 and a distal end 248. The proximal end 246 can extend into the expandable window 212. The proximal end 246 can be configured to engage the first arm 206. In some embodiments, the proximal end 246 may be rotatably engaged with the first arm 206. In other embodiments, the first and second arms 206, 208 may be configured for at least partial rotational and/or pivotal motion with respect to one another. As illustrated in FIG. 5A, in some embodiments, the proximal end 246 can include a gear member having teeth configured to mesh with gear teeth on the first arm 206. The distal end 248 may be pivotably coupled to the second elongate body 204. For example, the first arm 208 may be configured to pivot about a pin 250 that is coupled to both the second arm 208 and the second elongate body 204. The second arm 208 may be configured to pivot in a plane (e.g., a horizontal plane) that is parallel to a plane defined by both the first and second elongate bodies 202, 204. The second arm 208 may be configured to pivot about an axis that is perpendicular to the length of the first elongate body 202 and/or parallel to the axis about which the first arm 206 may pivot. In some embodiments, the second arm 208 may be coupled to the superior surface 220 of the second elongate body 204. In other embodiments, the second arm 208 may be coupled to the inner side surface 236 and/or disposed within the elongate slot or groove (not shown). In yet other embodiments, the second arm 208 may be coupled to the inferior surface (not shown) of the second elongate body 204. In some embodiments, the second arm 208 may be coupled to the second elongate body 204 in the same place that the first arm 206 is coupled to the first elongate body 202. For example, as illustrated in FIG. 5A, the first and second arms 206, 208 may each be coupled to the superior surfaces 220, 234 of the first and second elongate bodies 202, 204. The second arm 208 may be coupled to the second elongate body 204 anywhere along the length thereof. As illustrated in FIG. 5A, the second arm 208 may be aligned with the first arm 206 along the length of the implant 200.

In some embodiments, the expandable spinal implant 200 may include at least one pair of arms. As illustrated in FIG. 5A, the expandable spinal implant 200 may include more than one pair of arms. For example, the expandable spinal implant 200 can include two, three, four, or more pairs of arms. As illustrated in FIG. 5A, the expandable spinal implant 200 can include three pairs (e.g., leading, central, and trailing), or a total of six arms. In some embodiments, each arm in a pair may be identical to the other arm in the pair. In other embodiments, one pair of arms may have different features as compared to another pair of arms on the expandable spinal implant 200. For example, the trailing pair (e.g., including first and second arms 206, 208) may include bent arms, the central pair (e.g., including third and fourth arms 252, 254) may include straight arms, and the leading pair (e.g., including fifth and sixth arms 256, 258) may include straight arms. Additionally, in some embodiments, each pair of arms may be coupled to different surfaces of the first and second elongate bodies 202, 204. For example, the trailing and leading pairs may be coupled to the superior surfaces 220, 234, and the central pair may be disposed within a slot on the inner surfaces of the first and second elongate bodies 202, 204.

The connector member may be configured for linear translation, e.g., along the length of the implant 200. The connector member may be generally thin and flat, and can include at least two holes, each configured to receive a pin therethrough. In some embodiments, the connector member may be configured to translate towards and/or away from the leading and trailing ends of the implant 200. As illustrated in FIG. 5A, the implant 200 may include at least one connector member 210 coupled to the trailing pair of arms (e.g., first and second arms 206, 208). The connector member 210 may include a tab 266 or other extension member extending towards the trailing end of the implant 200. The tab 266 may be configured to engage an insertion tool as described further herein. The combination of the connector member 210 and the tab 266 may be referred to herein as an enlarged connector member. As illustrated in FIG. 5A, connector member 210 may be pivotably coupled to the proximal ends 240, 246 of the first and second arms 206, 208. In some embodiments, the implant 200 can include a pin 260 that is coupled to the connector member 210 and the first arm 206. The implant 200 can also include a pin 262 that is coupled to the connector member 210 and the second arm 208. The connector member 210 may be coupled to a superior or inferior surface of the first and/or second arms 206, 208. In some embodiments, the connector member 210 may be connected to one or more additional connector members. For example, as illustrated in FIG. 5A, the connector member 210 may be connected to connector member 263 via a stem 265. In some embodiments, all connector members of the implant 200 may be interconnected. In other embodiments, at least one connector member (e.g., connector member 210) may not be coupled to every other connector member of the implant 200. For example, as illustrated in FIG. 5A, the connector member 210 may not be connected to the connector member 264. Connector member 264 may be configured to pivotably couple two arms (e.g., fifth arm 256 and sixth arm 258).

Embodiments herein are also directed to methods of installing the expandable spinal implant 200. These embodiments can include providing the expandable spinal implant 200 in a collapsed (e.g., closed) configuration. In this configuration, the proximal end 240 of the first arm 206 may be pivoted towards the first elongate body 202 and/or the leading end 214. The proximal end 246 of the second arm 208 may be pivoted towards the second elongate body 204 and/or the leading end 230. When in the collapsed configuration, the expandable spinal implant 200 may have a first, collapsed width, as measured from the outer side surface 226 of the first elongate body 202 to the outer side surface 238 of the second elongate body 204.

In some embodiments, the step of providing the expandable spinal implant 200 in the collapsed configuration can include inserting the implant 200 into a selected location, such as a cavity between two vertebral bodies created by a discectomy or other procedure. In some embodiments, this step can include reversibly coupling the implant 200 to an insertion tool, and using the insertion tool to guide the implant 200 into the cavity. The implant 200 can be inserted into the cavity using a variety of approaches, such as anteriorly, posteriorly, transforaminally, or laterally. In some embodiments, the implant 200 may advantageously be configured to be inserted into an intervertebral space using a lateral procedure. Those skilled in the art may appreciate that, in some embodiments, when in the closed or collapsed configuration, the expandable spinal implant 200 may have a width that is about 50-65% less than the width in the expanded configuration. In some embodiments, the closed or collapsed width of the implant 200 may be about 55-60% less than the expanded width. In other embodiments, the closed or collapsed width of the implant 200 may be less than half of the expanded width thereof. Advantageously, the implant 200 may be inserted through a smaller, less-invasive opening that may result in reduced trauma to muscles, nerves, or other tissue. When used in a lateral procedure (e.g., lateral lumbar interbody fusion), the implant 200 may be inserted laterally in the far anterior side of the intervertebral space. This technique can advantageously reduce or minimize interaction with the posteriorly-located lumbar plexus.

These methods can also include translating the connector member 210 towards the trailing end 205 of the implant 200. This step can include grasping the tab 266 and pulling the tab 266 towards the trailing end. As the connector member 210 is translated towards the trailing end, the proximal ends 240, 246 of the first and second arms 206, 208 may also be translated towards the trailing end 205, thereby pushing apart the distal ends 242, 248, as illustrated in FIGS. 5A-B. The connector member 210 may be translated towards the trailing end 205 of the implant 200 until the implant 200 attains a second width that is greater than the first width. In some embodiments, the second width may be 100-150% greater than the first width. In other embodiments, the second width may be at least twice of the first width. In some embodiments, the connector member 210 may translate towards the trailing end 205 until the first arm 206 abuts the trailing end 216 of the first elongate body 202, as illustrated in FIG. 5B. In other embodiments, the connector member 210 may be translated towards the trailing end until the first arm 206 is perpendicular to the first elongate body 202 and/or the second arm 208 is perpendicular to the second elongate body 204. For example, the proximal ends 240, 246 may be fully extended away from the first and second elongate bodies 202, 204. Those skilled in the art may appreciate that in other embodiments, the first and second arms 206, 208 may be angled towards the trailing end when in the collapsed configuration. Accordingly, the implant 200 may be expanded by translating the connector member 210 towards the leading end, for example, by pushing the tab 266.

In some embodiments, the step of translating the connector member 210 can include manually (e.g., directly) grasping and applying force to the connector member 210 and/or tab 266. In other embodiments, this step can include reversibly coupling an insertion tool to the connector member 210. In some embodiments, the insertion tool can include a linearly-retractable arm that extends proximally from a grabbing member. Those skilled in the art may appreciate that, with respect to the insertion tool, the terms "proximal" and "distal" are utilized with reference to a user of the tool. The grabbing member may be configured to engage (e.g., grasp) the connector member 210 and/or tab 266 and may include, for example, a clamp, claw, or pincers. The grabbing member may be configured to pass at least partially through the channel 228 of the first elongate body 202. The insertion tool may also include a grabbing actuator engaged with and configured to actuate the grabbing member. For example, the grabbing actuator may cause the grabbing member to grasp and/or release the tab 266. The insertion tool may also include an arm actuator engaged with and configured to extend and/or retract the arm. One or both actuators may include a knob, button, switch, lever, and/or other user interface members. The insertion tool may also include a handle at a proximal end of the tool (e.g., extending proximally from the retractable arm). In some embodiments, the handle may house one or both actuators. The insertion tool may also include a docking member configured to reversibly engage the implant 200, as described herein. For example, the docking member may include a threaded rod that is configured to threadably engage the implant 200. In some embodiments, the insertion tool may also include a cannula extending longitudinally and/or axially therethrough. Advantageously, the cannula may be configured to transport bone graft material to the expandable window 212. The insertion tool may also include a driver (e.g., a screw driver) configured to engage the set screw disposed within the threaded hole of the trailing end 216 of the first elongate body 202.

In some embodiments, the step of coupling the insertion tool with the connector member 210 may include inserting the grabbing member into the expandable window 212 through the channel 228, and may further include actuating the grabbing member to grasp the tab 266. Subsequently, a force may be applied to the insertion tool to translate the connector member 210. The step of applying force to the insertion tool can include applying force to the arm actuator, thereby retracting the arm of the insertion tool, translating the connector member 210, and expanding the implant 200.

Methods herein may further include the step of securing or locking the implant 200 in the expanded configuration. This step can include threading the set screw through the threaded hole 229 at the trailing end 216 of the first elongate body 202 and into contact with the first arm 206. In some embodiments, the set screw may be engaged with the first arm 206 in an interference fit. Those skilled in the art may appreciate that the force applied by the set screw may prevent or inhibit the first arm 206 from returning to its collapsed orientation.

Bone graft material may also be inserted through the cannula of the insertion tool to the expandable window 212. In some embodiments, bone graft material may be inserted through the channel 228 and/or through a separate window on the first and/or second elongate bodies 202, 204. Thereafter, the insertion tool may be disengaged from the implant 200. This step may include releasing the connector member 210 and/or tab 266 and removing the grabbing member through the channel 228. This step may also include disengaging (e.g., unthreading and/or unlocking) the insertion tool from the implant 200.

Turning now to FIGS. 6A-E, some embodiments herein are directed to an expandable spinal implant 400 that can include a first elongate body 402, a second elongate body 404, and a first expansion assembly 406. The expandable spinal implant 400 may include a length defined between a leading end 403 and a trailing end 405. The expandable spinal implant 400 may also include a width defined between an outer side surface 414 of the first elongate body 402 and an outer side surface 426 of the second elongate body 404. The expandable spinal implant 400 may advantageously be configured to transition reversibly between an expanded configuration and a collapsed configuration. The implant 400 may have a width in the expandable configuration that is greater than a width in the collapsed configuration. In some embodiments, the implant 400 may have a collapsed width in the range of from about 10 mm to about 15 mm, and an expanded width in the range of from about 25 mm to about 30 mm.

Figure 6B:
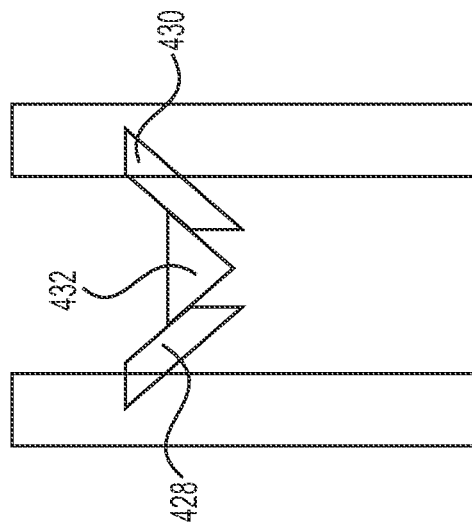
FIGS. 6A-D illustrate schematic views of one embodiment of an expandable spinal implant described herein.
Figure 6A:
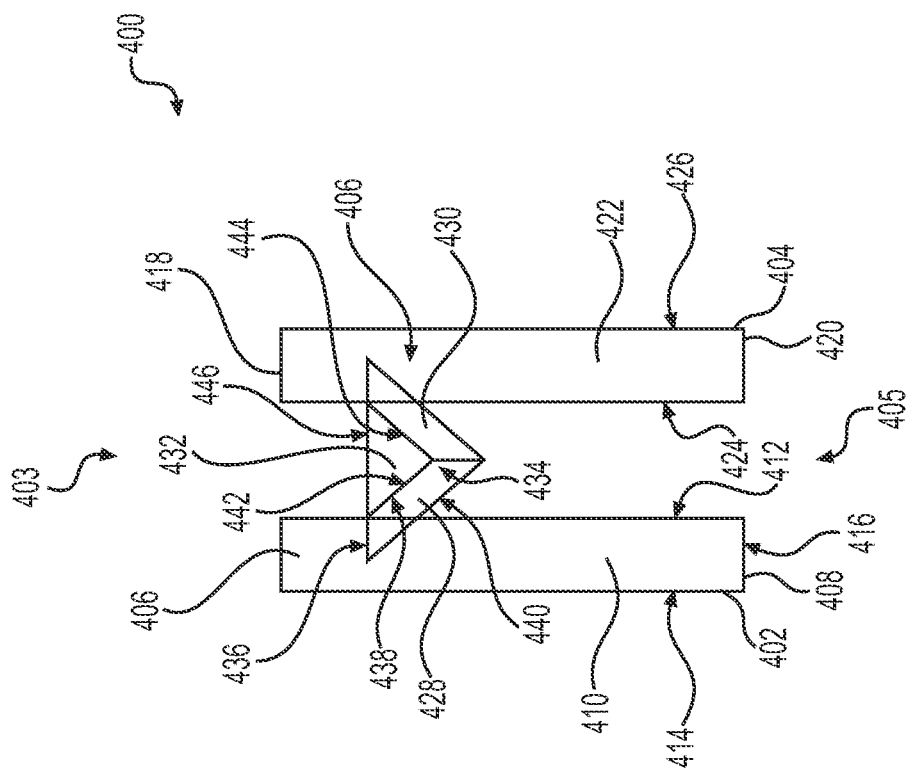

As illustrated in FIG. 6A, the first elongate body 402 can include a leading end 406 and a trailing end 408. The first elongate body 402 may have a length as measured between the leading end 406 and the trailing end 408. Although not limited to any particular orientation, in some embodiments the first elongate body 402 may be configured for anterior orientation in a patient and may thus be referred to as an anterior elongate body. The first elongate body 402 can include a superior surface 410, an inferior surface opposite the superior surface 410 (not shown), an inner side surface 412, and an outer side surface 414. In some embodiments, at least a portion of the inner side surface 412 may include an elongate guide member (e.g., a groove, channel, rail, slot, and/or track) (not shown) extending longitudinally thereon. The elongate guide member may be configured to engage the first expansion assembly 406 or a portion thereof, as described herein. The inner side surface 412 may also include a locking member (not shown), such as a stop or bump, configured to inhibit translation of the first expansion assembly 406 beyond the locking member. The first elongate body 402 may have a width as measured between the inner side surface 412 and the outer side surface 414. In some embodiments, the width of the first elongate body 402 may be generally equal to one-half of the width of the implant 400 in the collapsed configuration. In some embodiments, the outer side surface 414 may be convex, as viewed from the superior and/or inferior surfaces. The superior surface 410 and/or inferior surface may be convex, as viewed from the outer side surface 414, leading end 406, and/or trailing end 408. In other embodiments, the superior surface 410 and/or inferior surface may be angled and/or slanted, such that the height of the first elongate body 402 is greater at the outer side surface 414 than at the inner side surface 412. As described herein, the superior and/or inferior surfaces may include a plurality of texturizing members.

In some embodiments, the leading end 406 of the first elongate body 402 may be tapered. For example, the leading end 406 can include a tapered height (e.g., as measured between the superior surface 410 and the inferior surface) and/or a tapered width (e.g., as measured between the inner side surface 412 and the outer side surface 414). In use, the tapered leading end 406 may advantageously be configured to distract tissue during insertion.

In some embodiments, the first elongate body 402 may have a generally constant width. In other embodiments, the width of the trailing end 408 may be generally equal to the width of the leading end 406. In some embodiments, the first elongate body 402 may include a longitudinal cavity 416 extending at least partially therethrough. The longitudinal cavity 416 may include an opening at the trailing end 408 of the first elongate body 402. The longitudinal cavity 416 may be configured to receive a tool, such as a driver, therethrough. In some embodiments, the longitudinal cavity 416 may include a locking member, such as a pin or protrusion, configured to restrain the tool therein. In some embodiments, the longitudinal cavity 416 may be cylindrical (e.g., may include a constant, circular diameter). The longitudinal cavity 416 may pass through (e.g., may not intersect) the superior surface 410 and/or inferior surface. In some embodiments, the longitudinal cavity 416 may intersect one or more additional passageways of the implant 400. In some embodiments, the first wedge member 432, described further herein, may be accessible through the longitudinal cavity 416 of the first elongate body 402. The trailing end 408, or other portion of the first elongate body 402, may also include one or more windows configured to receive bone growth material therethrough.

As illustrated in FIG. 6A, the second elongate body 404 can include a leading end 418 and a trailing end 420. The second elongate body 404 may have a length as measured between the leading end 418 and the trailing end 420. The length of the second elongate body 404 may be generally equal to the length of the first elongate body 402. Although not limited to any particular orientation, in some embodiments the second elongate body 404 may be configured for posterior orientation in a patient and may thus be referred to as a posterior elongate body. The second elongate body 404 can include a superior surface 422, an inferior surface opposite the superior surface 422 (not shown), an inner side surface 424, and an outer side surface 426. In some embodiments, at least a portion of the inner side surface 424 may include an elongate guide member (e.g., a groove, channel, rail, slot, and/or track) (not shown) extending longitudinally thereon. The elongate guide member may be configured to engage the first expansion assembly 406 or a portion thereof, as described herein. The inner side surface 424 may also include a locking member (not shown), such as a stop or bump, configured to inhibit translation of the first expansion assembly 406 beyond the locking member. The second elongate body 404 may have a width as measured between the inner side surface 424 and the outer side surface 426. The width of the second elongate body 404 may be less than, greater than, or equal to the width of the first elongate body 402. In some embodiments, the width of the second elongate body 404 may be generally equal to one-half of the width of the implant 400 in the collapsed configuration. In some embodiments, at least a portion of the outer side surface 426 may be straight or generally straight (e.g., non-curved), as viewed from the superior and/or inferior surfaces. The superior surface 422 and/or inferior surface may be convex, as viewed from the outer side surface 426, leading end 418, and/or trailing end 420. In other embodiments, the superior surface 422 and/or inferior surface may be angled and/or slanted, such that the height of the second elongate body 404 is less at the outer side surface 426 than at the inner side surface 424. In some embodiments, the second elongate body 404 may have a maximum height that is less than a maximum height of the first elongate body 402, so as to match the natural lordosis of a spine. In these embodiments, the expandable spinal implant 400 may be wedge-shaped. In other embodiments, the expandable spinal implant 400 may have a constant height. As described herein, the superior and/or inferior surfaces may include a plurality of texturizing members.

Figure 6D:
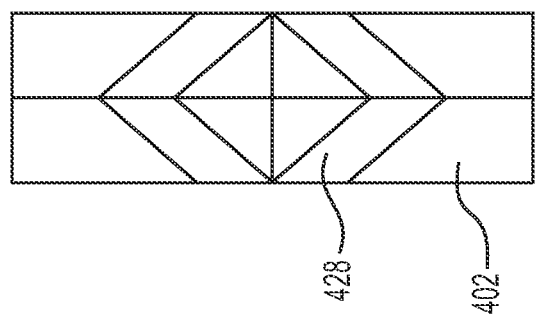

As illustrated in FIG. 6A, the first expansion assembly 406 can include a first (e.g., anterior) ramp member 428, a second (e.g., posterior) ramp member 430, and a first wedge member 432. The first ramp member 428 may be configured to slideably engage the first elongate body 402 and/or the first wedge member 432. The first ramp member 428 can include a proximal surface 434, a distal surface 436, an inner surface 438, and an outer surface 440. The inner and outer surfaces 438, 440 may be parallel to each other. In some embodiments, the proximal and distal surfaces 434, 436 may be perpendicular to each other. In these embodiments, the first ramp member 428 may be trapezoidal. In other embodiments, the proximal and distal surfaces 434, 436 may be parallel to each other. In these embodiments, the first ramp member 428 may be parallelogram-shaped. The first ramp member 428 may have a width that is not greater than the width of the first elongate body 402, for example, as illustrated in FIG. 6D. Furthermore, as illustrated in FIG. 6D, when in the collapsed configuration, the first ramp member 428 may occupy no more than half of the width of the implant 400. In some embodiments, the proximal surface 434 may be generally parallel to the length of the first and/or second elongate bodies 402, 404. In other embodiments, the proximal surface 434 may be generally perpendicular to the length of the first and/or second elongate bodies 402, 404. The distal and/or outer surfaces 436, 440 may include a corresponding mating feature, such as a tab or protrusion, configured to engage the guide member of the first elongate body 402.

The first ramp member 428 may include an axis that extends parallel to the inner and outer surfaces 438, 440. In some embodiments, the axis of the first ramp member 428 may extend at an angle away from the first elongate body 402. For example, the angle may be in the range of from about 10 degrees to about 80 degrees. In some embodiments, the angle may be in the range of from about 30 degrees to about 60 degrees. In some embodiments, the first ramp member 428 may be angled towards the trailing end 405 of the implant 400, for example, as illustrated in FIG. 6A. In other embodiments, the first ramp member 428 may be angled towards the leading end 403. In some embodiments, the inner surface 438 of the first ramp member 428 may include an elongate guide member (e.g., a groove, channel, rail, slot, and/or track) (not shown) extending longitudinally thereon. The elongate guide member may be configured to slideably engage the first wedge member 432. The inner surface 438 may also include a locking member (not shown), such as a stop or bump, configured to inhibit translation of the first wedge member 432 beyond the locking member. In some embodiments, the inner and/or outer surfaces 438, 440 may include at least one retention member, such as a ratchet or angled tooth, that can be configured to inhibit translation of the first ramp member 428 and/or the first wedge member 432 in one direction (e.g., towards the leading end 403).

The second ramp member 430 can be configured to slideably engage the second elongate body 404 and/or the first wedge member 432. The second ramp member 430 can include some or all of the same features as the first ramp member 428. In some embodiments, the second ramp member 430 may be symmetrical to and/or may be a mirror image of the first ramp member 428.

The first wedge member 432 may be configured to slideably engage the first and second ramp members 428, 430. As illustrated in FIG. 6A, the first wedge member 432 may include an anterior surface 442, a posterior surface 444, and a lateral surface 446. Those skilled in the art may appreciate that these and other directional terms herein are used for descriptive purposes and do not limit the orientation in which any of the expandable spinal implants described herein may be used. As illustrated in FIG. 6A, the first wedge member 432 may include a triangular cross-section. The anterior surface 442 may be configured to engage a portion of the first ramp member 428 (e.g., inner surface 438) and the posterior surface 444 may be configured to engage a portion of the second ramp member 430 (e.g., an inner surface thereof). The anterior and/or posterior surfaces 442, 444 may include a mating feature, such as a tab or protrusion, configured to engage the elongate guide members on the inner surfaces of the first and second ramp members 428, 430. In some embodiments, the anterior and/or posterior surfaces 442, 444 may include at least one retention member, such as a ratchet or angled tooth, that can be configured to inhibit translation of the first wedge member 432 in one direction (e.g., towards the leading end 403).

The first wedge member 432 may include an anterior angle between the anterior surface 442 and the lateral surface 446, and a posterior angle between the posterior surface 444 and the lateral surface 446. In some embodiments, the anterior angle may be equal to the posterior angle. In other embodiments, the anterior angle may be greater than or less than the posterior angle. In some embodiments, the angle between the anterior and posterior surfaces 442, 444 may be generally equal to an angle between the inner surfaces of the first and second ramp members 428, 430, when the first and second ramp members are in contact with each other (e.g., when the proximal walls are in contact with each other). The first wedge member 432 may have a width that is equal to a width of the lateral surface 446 between the anterior and posterior surfaces 442, 444. In some embodiments, the width of the first wedge member 432 may not be more than twice the width of the first elongate body 402. In some embodiments, the width of the first wedge member 432 may not be greater than the width of the implant 400.

Figure 6C:
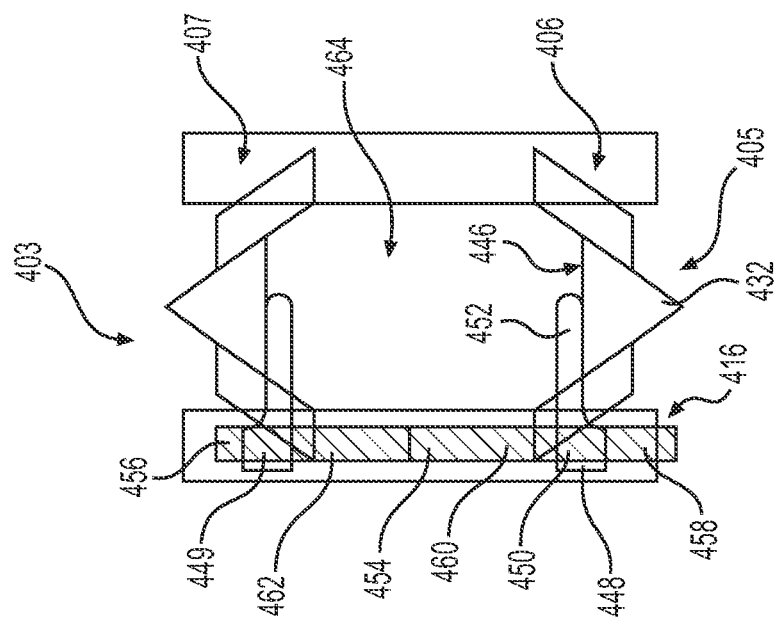

In some embodiments, the expandable spinal implant 400 may include one expansion assembly. In other embodiments, the expandable spinal implant 400 may include two, three, four, or more expansion assemblies. As illustrated in FIG. 6C, the expandable spinal implant 400 can include first expansion assembly 406 and second expansion assembly 407. In some embodiments, the expansion assemblies may be configured to translate in the same direction and/or the wedge members may be pointed towards the same end (e.g., towards the trailing end 405 or leading end 403). In other embodiments, the expansion assemblies may be configured to translate in different directions, and/or the wedge members may be pointed in opposite directions. For example, as illustrated in FIG. 6C, the first expansion assembly 406 may be configured to translate towards the trailing end 405 and the second expansion assembly 407 may be configured to translate towards the leading end 403.

Figure 6E:
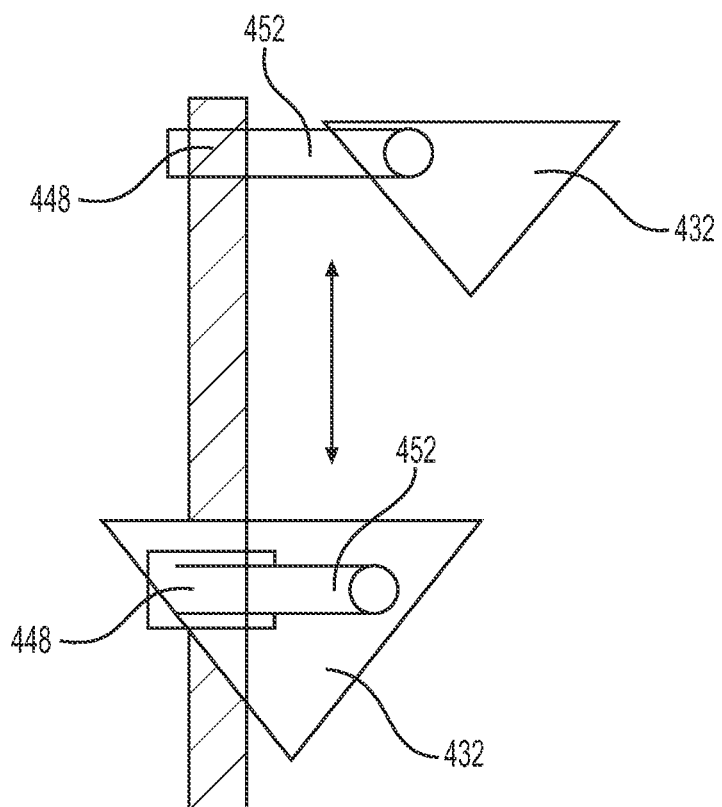
FIG. 6E illustrates a schematic view of one embodiment of a wedge member described herein.

In some embodiments, the expandable spinal implant 400 may further include a first collar 448 configured to engage the first expansion assembly 406 or a portion thereof (e.g., the first wedge member 432), as illustrated in FIG. 6C. The first collar 448 may include a distal end 450 disposed within the longitudinal cavity 416 and a proximal end 452 configured to engage the first wedge member 432. The distal end 450 may include a threaded hole extending therethrough and configured to be coaxial with the longitudinal cavity 416. The first collar 448 may be in slideable engagement with the first wedge member 432. As illustrated in FIG. 6C, in some embodiments, the first collar 448 may be engaged with the lateral surface 446 of the first wedge member 432. In other embodiments, the first wedge member 432 may include a receptacle configured to receive the proximal end 452 of the first collar 448 therein, for example, as illustrated in FIG. 6E. As described herein, in some embodiments, the expandable spinal implant 400 may include two or more expansion assemblies. The implant 400 may also include a separate collar for each expansion assembly. For example, as illustrated in FIG. 6C, implant 400 includes first and second expansion assemblies 406, 407 and first and second collars 448, 449.

In some embodiments, the expandable spinal implant 400 may further include an elongate rod 454 configured to be housed and/or disposed within the longitudinal cavity 416 of the first elongate body 402, for example, as illustrated in FIG. 6C. The elongate rod 454 may be configured to rotate within the longitudinal cavity 416. The elongate rod 454 may include a leading end 456 and a trailing end 458. The trailing end 458 may include a tool-engaging surface configured to engage a driver. For example, the trailing end 458 may include a socket configured to couple with a driver, such as a hexagonal, star, Phillips, and/or slotted. The elongate rod 454 may include a first threaded section 460 between the leading and trailing ends 456, 458. In some embodiments that include two expansion assemblies, the elongate rod 454 may also include a second threaded section 462 between the leading and trailing ends 456, 458. The threads of the first section 460 may extend in a direction opposite the threads of the second section 462 (e.g., clockwise and counterclockwise, or vice versa). The first threaded section 460 may be configured to engage the first collar 448 and the second threaded section 462 may be configured to engage the second collar 449. In some embodiments, the first elongate body 402 may include at least one retention member, such as a pin or keyed hole, which may be configured to inhibit longitudinal translation of the elongate rod 454 within the longitudinal cavity 416. In some embodiments, the elongate rod 454 may include a receptacle, such as a circumferential groove or undercut, that may be configured to receive or engage the retention member.

Embodiments herein are also directed to methods of installing the expandable spinal implant 400. These methods can include providing the expandable spinal implant 400 in the collapsed configuration, for example, as illustrated in FIG. 6D.

In some embodiments, the step of providing the expandable spinal implant 400 in the collapsed configuration can include inserting the implant 400 into a selected location, such as a cavity between two vertebral bodies created by a discectomy or other procedure. In some embodiments, this step can include reversibly coupling the implant 400 to an insertion tool, and using the insertion tool to guide the implant 400 into the cavity. The implant 400 can be inserted into the cavity using a variety of approaches, such as anteriorly, posteriorly, transforaminally, or laterally. In some embodiments, the implant 400 may advantageously be configured to be inserted into an intervertebral space using a lateral procedure. Those skilled in the art may appreciate that, in some embodiments, when in the closed or collapsed configuration, the expandable spinal implant 400 may have a width that is about 50-65% less than the width in the expanded configuration. In some embodiments, the closed or collapsed width of the implant 400 may be about 55-60% less than the expanded width. In other embodiments, the closed or collapsed width of the implant 400 may be less than half of the expanded width thereof. Advantageously, the implant 400 may be inserted through a smaller, less-invasive opening that may result in reduced trauma to muscles, nerves, or other tissue. When used in a lateral procedure (e.g., lateral lumbar interbody fusion), the implant 400 may be inserted laterally in the far anterior side of the intervertebral space. This technique can advantageously reduce or minimize interaction with the posteriorly-located lumbar plexus.

In embodiments where the expandable spinal implant 400 includes the elongate rod 454, these methods can also include rotating the elongate rod 454. This step can include engaging the elongate rod 454, for example, with a driver such as a hex key. The driver may be part of the insertion tool. Torque may then be applied to the driver, thereby rotating the elongate rod 454. As the elongate rod 454 rotates, the first collar member 448 may translate along the elongate rod 454 in a first direction, e.g., towards the trailing end 405. The first collar 448 may urge the first wedge member 432 to translate in the same direction, thus urging and/or pushing the first and second ramp members 428, 430 apart, and consequently separating the first and second elongate bodies 402, 404 until the implant 400 attains a second, expanded width that is greater than the closed or collapsed width, as illustrated in FIG. 6B. In some embodiments, as the first wedge member 432 is translated towards the leading and/or trailing ends 403, 405, the first wedge member 432 may also slide along the proximal end 452 of the first collar 448, as illustrated in FIG. 6E.

In some embodiments, the expandable spinal implant 400 can also include second expansion assembly 407, and the elongate rod 454 can also include second threaded section 462, as illustrated for example in FIG. 6C. In these embodiments, as the elongate rod 454 rotates, the first collar 448 may translate along the elongate rod 454 in a first direction, e.g., towards the trailing end 405, and the second collar 449 may translate along the elongate rod 454 in a second direction, e.g., towards the leading end 403. The first collar 448 may urge the first wedge member 432 to translate in the first direction and the second collar 449 may urge a second wedge member of the second expansion assembly 407 to translate in the second direction. As illustrated in FIG. 6C, the first and second expansion assemblies may translate away from each other as the implant 400 expands, thereby creating a cavity 464 therebetween.

In other embodiments, the expandable spinal implant 400 may not include elongate rod 454. In these embodiments, the implant 400 can be expanded using a driver (not shown). The driver can include an elongate rod assembly that can include a leading end, a trailing end, and a first threaded section between the leading and trailing ends. Methods of installing the expandable spinal implant 400 can include providing the implant in the collapsed configuration as described herein and inserting the driver into the longitudinal cavity 416. The methods can also include coupling the first threaded section of the elongate rod assembly with the first collar 448. The driver can also be coupled to the first elongate body 402, for example, to inhibit longitudinal translation of the driver. The methods can also include rotating the elongate rod assembly, thereby translating the first collar 448 and the first wedge member 432, and urging the first and second elongate bodies 402, 404 apart until the implant 400 attains an expanded width that is greater than the collapsed width.

In embodiments where the expandable spinal implant 400 includes second expansion assembly 407, the elongate rod assembly can additionally include a second threaded section between the leading and trailing ends. In these embodiments, the method of installing the implant 400 can also include coupling the second end of the elongate rod with the second collar 449 prior to rotating the elongate rod assembly. In some embodiments, the threads of the first section can extend in a direction opposite the threads of the second section (e.g., clockwise and counterclockwise, or vice versa). In other embodiments, they can extend in the same direction.

In some embodiments, the elongate rod assembly can include a first rod member concentrically disposed within a cannula of a second rod member. The first threaded section may be disposed on the first rod member and the second threaded section may be disposed on the second rod member. The first rod member may be configured to extend and retract from within the second rod member. The first and second rod members may be configured to rotate independently of each other. In these embodiments, the step of rotating the elongate rod assembly can include rotating the first rod member to translate the first wedge member 432 in a first direction and rotating the second rod member to translate the second wedge member in a second direction.

In some embodiments, the method can further include locking or securing the expandable implant 400 in the expanded configuration. This step can include threading a set screw into the implant 400 to block or prevent the one or more expansion assemblies from retracting to their collapsed positions. In other embodiments, one or more components of the implant 400 may include a retention member, such as a ratchet or angled tooth, which may be configured to prevent the one or more expansion assemblies from retracting. In yet other embodiments, the implant 400 may be self-locking.

Some methods herein can further include disengaging the insertion tool and/or driver from the implant 400. In embodiments that include the elongate rod 454, this step can include disengaging the insertion tool from the elongate rod 454. In embodiments that do not include the elongate rod 454, this step can include disengaging (e.g., unthreading) the driver from the first and second collars 448, 449. Methods herein can also include inserting bone graft material into the cavity 464. In some embodiments, this step may be accomplished before the insertion tool and/or driver is disengaged from the implant 400. In these embodiments, the insertion tool and/or driver may include a cannula through which the bone graft material may be transported to the implant 400, for example, via the longitudinal cavity 416. In other embodiments, the bone graft material may be inserted after the insertion tool and/or driver is removed. In these embodiments, the bone graft material may be inserted, e.g., through the longitudinal cavity 416 and/or through a graft window on at least one of the first and second elongate bodies 402, 404.

Figure 7A:
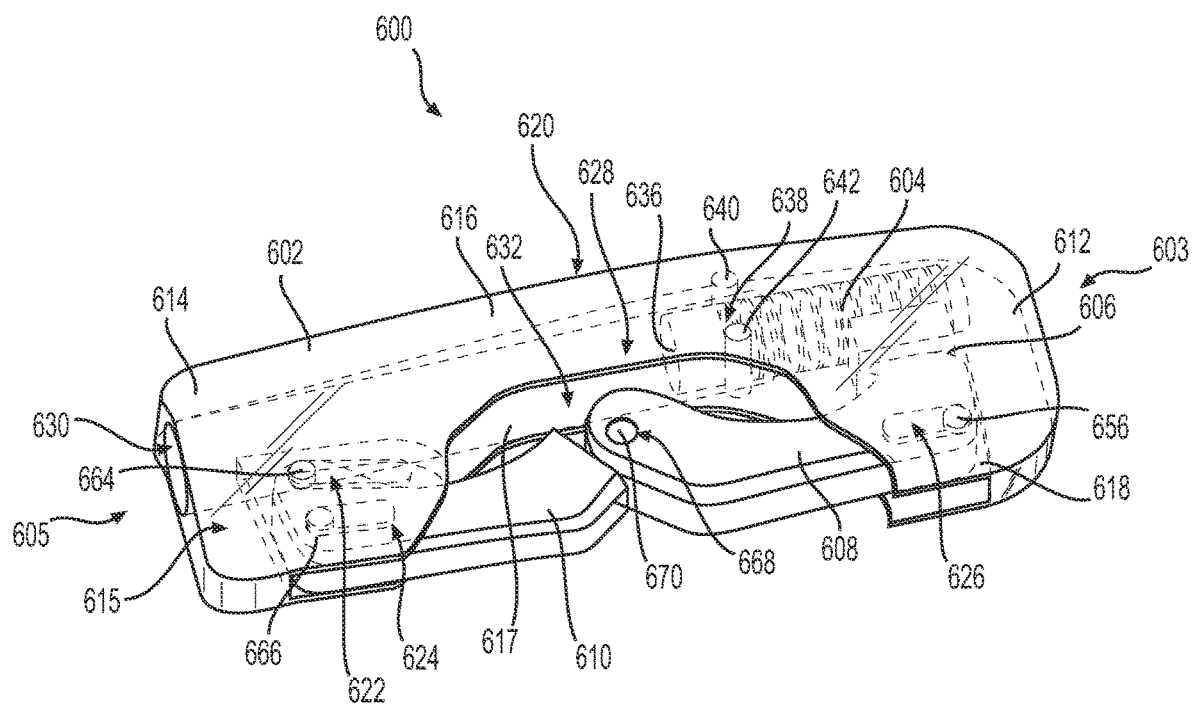
FIGS. 7A-C illustrate perspective views of one embodiment of an expandable spinal implant described herein
Figure 7B:
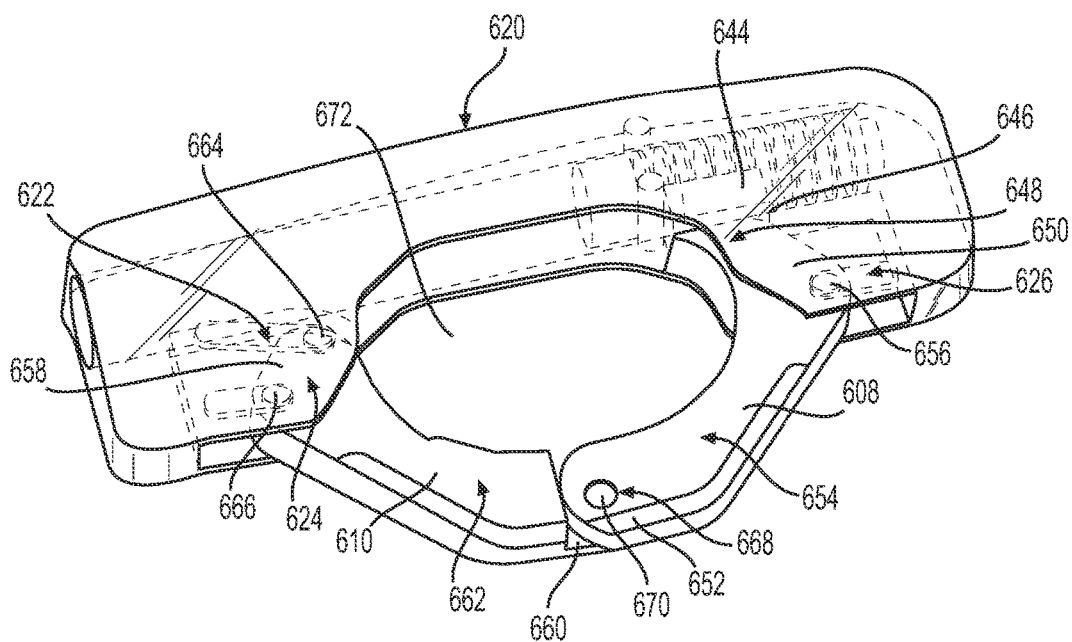
Figure 7C:
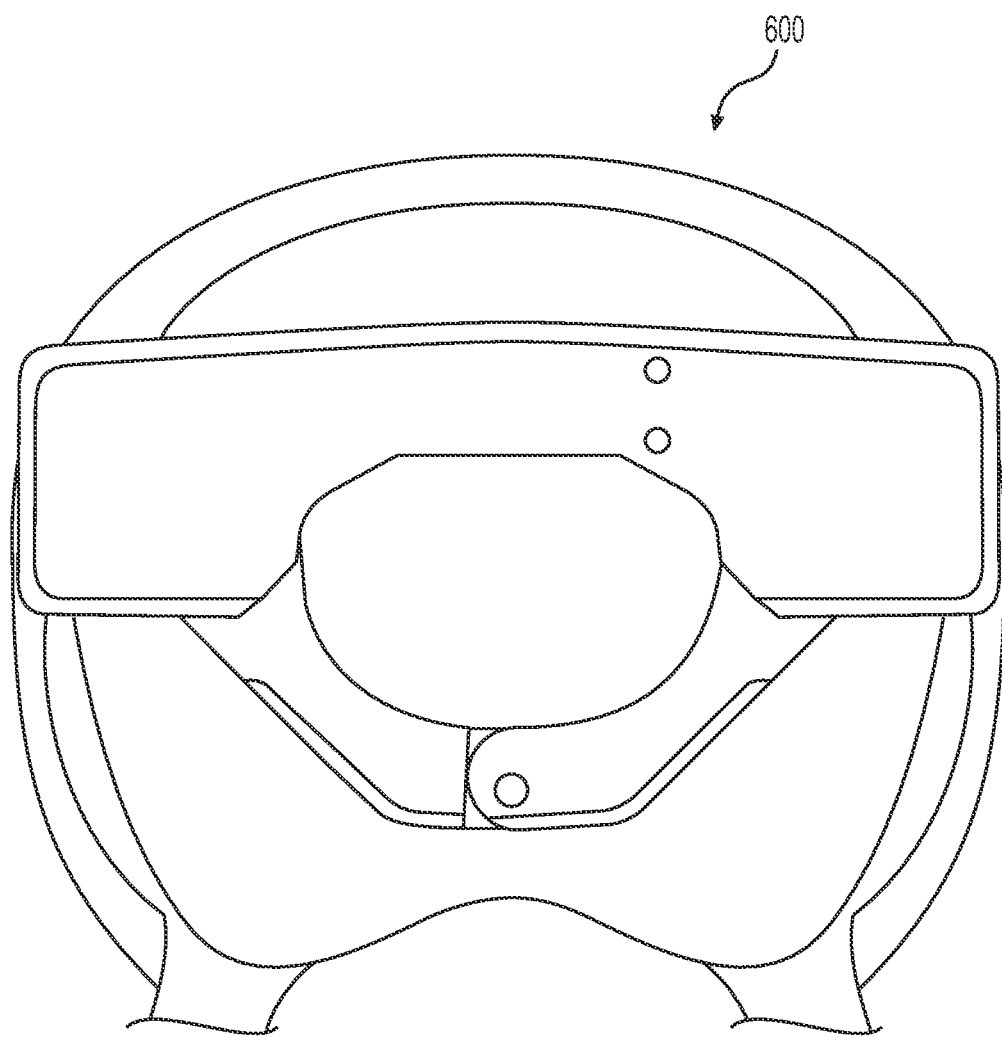

Turning now to FIGS. 7A-C, some embodiments herein are directed to an expandable spinal implant 600 that can include an elongate body 602, a first (e.g., leading) arm 608, and a second (e.g., trailing) arm 610. The expandable spinal implant 600 may include a length defined between a leading end 603 and a trailing end 605. The expandable implant 600 may also include a width defined from an anterior side surface 620 of the elongate body 602 to a medial end of the first and/or second arms 608, 610, as illustrated in FIG. 7B. The expandable spinal implant 600 may advantageously be configured to transition reversibly between an expanded configuration and a collapsed configuration. The implant 600 may have a width in the expandable configuration that is greater than a width in the collapsed configuration.

As illustrated in FIG. 7A, the elongate body 602 can include a first (e.g., leading) end 612 and a second (e.g., trailing) end 614. The elongate body 602 may have a length as measured between the first end 612 and the second end 614. The second end 614 may be configured to engage an insertion tool. As illustrated in FIG. 7A, the second end 614 may include a threaded receptacle 615 configured to threadably engage the insertion tool. The elongate body 602 may include an upper wall 616, a lower wall 617 opposite the upper wall, a posterior side surface 618, and an anterior side surface 620. Those skilled in the art may appreciate that these and other directional terms herein are used for descriptive purposes and do not limit the orientation in which any of the expandable spinal implants described herein may be used. The elongate body 602 may have a width as measured between the anterior side surface 620 and the posterior side surface 618. In some embodiments, the width of the elongate body 602 may be generally equal to the width of the implant 600 in the collapsed configuration. In some embodiments, the elongate body 602 may include a cutout 632 that passes through the upper wall 616, lower wall 617, and/or posterior side surface 618. Accordingly, the cutout 632 may define a posterior opening along the posterior side surface 618. In some embodiments, the anterior side surface 620 may be convex, as viewed, for example, from the upper wall 616 and/or lower wall 617. The upper and/or lower walls 616, 617 may extend between the first end 612 and the second end 614. The elongate body 602 may be at least partially hollow. The upper wall 616 may include a superior (e.g., outer) and/or inferior (e.g., inner) surface. The lower wall 617 may also include a superior (e.g., inner) surface and/or an inferior (e.g., outer) surface. As described herein, the outer surfaces of the upper and/or lower walls 616, 617 may include a plurality of texturizing members. In some embodiments, the outer surfaces of the upper and/or lower walls 616, 617 may be convex, as viewed from the anterior side surface 620, posterior side surface 618, leading end 612, and/or trailing end 614. In other embodiments, the outer surfaces of the upper and/or lower walls 616, 617 may be angled and/or slanted, such that the height of the elongate body 602 is greater at the anterior side surface 620 than at the posterior side surface 618. In these embodiments, the expandable spinal implant 600 may be wedge-shaped. In other embodiments, the expandable spinal implant 600 may have a constant height.

In some embodiments, the elongate body 602 may be tapered at the leading end 612. For example, the leading end 612 can include a tapered height (e.g., as measured between the outer surfaces of the upper wall 616 and the lower wall 617) and/or a tapered width (e.g., as measured between the anterior side surface 620 and the posterior side surface 618). In use, the tapered leading end 612 may advantageously be configured to distract tissue during insertion.

The inferior surface of the upper wall 616 and/or the superior surface of the lower wall 617 can include one or more guide members (e.g., a groove, channel, rail, slot, track, rack, and/or pinion). In some embodiments, the guide member(s) on the upper wall 616 may be parallel to the guide member(s) on the lower wall 617. The guide member (s) may be straight or curved. In some embodiments, one or more guide member(s) can be located at the leading and/or trailing ends 612, 614. For example, the inferior surface can include first and second grooves 622, 624 at the trailing end 614, as illustrated in FIGS. 7A-B. In some embodiments, the first groove 622 may be an anterior groove and the second groove 624 may be a posterior groove. The first and second grooves 622, 624 may be parallel or non-parallel to each other. In some embodiments, the first and/or second grooves 622, 624 may extend along an axis that is parallel to a longitudinal axis of the implant 600. As illustrated in FIGS. 7A-B, the first and second grooves 622, 624 may be separated by a distance that decreases towards the leading end 612. The first and second grooves 622, 624 may each have a first end closer to the trailing end 614 and a second end closer to the leading end 612. In some embodiments, the first and second grooves 622, 624 may be separated by a distance that decreases towards the leading end 612. The inferior surface of the upper wall 616 can also include a groove 626 at the leading end 612. The groove 626 may extend along an axis parallel to the longitudinal axis of the implant 600.

The elongate body 602 may include a passageway 628 extending at least partially along the length thereof. The passageway 628 may also include an opening 630 at the trailing end 614 of the elongate body 602. The passageway 628 may pass between (e.g., may not intersect) the upper and lower walls 616, 617. The passageway 628 may be in fluid communication with the cutout 632. As illustrated in FIGS. 7A-B, the implant 600 may also include an actuator 604. The actuator 604 may be housed within the elongate body 602. In some embodiments, the actuator may be disposed within the passageway 628. The actuator 604 may be configured to activate the first and second arms as described herein. In some embodiments, the actuator 604 may include a rod having a threaded section and/or a non-threaded section. The actuator 604 may also include a tool-engaging surface 636 at a trailing end thereof. For example, the tool-engaging surface 636 can include a socket for coupling a driver, such as a hexagonal, star, Phillips, and/or slotted driver. The actuator 604 may be configured to rotate within the passageway 628 along a longitudinal axis thereof. In some embodiments, the rod 634 may further include a circumferential groove 638. In some embodiments, the implant 600 may include one or more retention members configured to inhibit translation of the actuator 604 along the passageway 628. For example, as illustrated in FIG. 7A, the implant 600 may include first and second pins 640, 642. The first and second pins 640, 642 may be configured to be received within the circumferential groove 638. In some embodiments, the first and second pins 640, 642 may each have a height that is not greater than the height of the implant 600, and may advantageously not increase the profile thereof.

In some embodiments, the expandable spinal implant 600 may also include a translatable connector 606. The translatable connector 606 may be configured to engage the actuator 604 and translate relative thereto. The translatable connector 606 may also be configured to engage the first arm 608. As illustrated in FIG. 7B, the translatable connector 606 may include a body portion 644 and an arm portion 646. The body portion 644 may include partially-threaded section, such as a threaded, U-shaped channel. The threaded, U-shaped channel may be configured to threadably mate with the threaded section of the actuator 604. The translatable connector 606 may also include a slot 648. As illustrated in FIG. 7B, the slot 648 may be disposed within the arm portion 646 of the translatable connector 606. The slot 648 may extend entirely through the translatable connector 606. For example, the slot 648 may have a length that extends from a top surface to a bottom surface of the translatable connector 606. The slot 648 may include a longitudinal axis that is perpendicular to the axis of the U-shaped channel. The slot 648 may also have an elongate cross-sectional shape. The slot 648 may define a path having a first end and a second end, wherein the second end is posterior to the first end. The slot 648 may be configured to receive a portion of the first arm 608 therein. In some embodiments, the first arm 608 may be configured to translate along the path defined by the slot 648.

The first arm 608 may be pivotably coupled to the translatable connector 606. The first arm 608 may also be pivotably, translationally, and/or slideably coupled to the elongate body 602, for example, at the first end 612. The first arm 608 may include a lateral end 650 and a medial end 652, as illustrated in FIG. 7B. The first arm 608 may also include a superior surface 654 and an inferior surface (not shown) opposite of the superior surface 654. In some embodiments, the first arm 608 may be a unitary body. In other embodiments, the first arm 608 may include multiple pieces or segments. The lateral end 650 of the first arm 608 may be coupled to the translatable connector 606 and/or the elongate body 602. The lateral end 650 may include a post. The post may be configured to be received within the slot 648 of the translatable connector 606. As described herein, the post may be configured to translate reversibly along the path defined by the slot 648.

In some embodiments, the first arm 608 may include at least one protrusion (e.g., bump, tab, and/or gear member) on a superior and/or inferior surface thereof. For example, the first arm 608 may include protrusion 656 on the superior surface 654 and at the lateral end 650 thereof. The protrusion may be configured to engage and/or mate with one of the guide members on the elongate body 602. As illustrated in FIGS. 7A-B, the protrusion 656 may be configured to be received within the groove 626 at the leading end 612 of the elongate body 602. The first arm 608 may include another protrusion on the inferior surface and at the lateral end 650 thereof. This protrusion may be configured to be received within a groove on the superior (e.g., inner) surface of the lower wall 617 of the elongate body 602. In use, those skilled in the art may appreciate that the protrusion 656 (alone or in combination with one or more protrusions on the inferior surface) may guide the first arm 608 along the path defined by the groove 626, and may enable to the first arm 608 to pivot relative thereto. Additionally, those skilled in the art may appreciate that in other embodiments, the elongate body 602 may include one or more protrusions and the first and/or second arms 608, 610 may include one or more guide members. The first arm 608 may include curved or angled anterior (e.g., inner) and/or posterior (e.g., outer) surfaces. For example, as illustrated in FIGS. 7A-B, the first arm 608 can include a curved anterior surface and an angled posterior surface. The first arm 608 may have a height that is not greater than the height of the elongate body 602. When the implant 600 is in the collapsed configuration, the first arm 608 may be configured to not protrude beyond the anterior and/or posterior side surfaces 620, 618 of the elongate body 602.

The second arm 610 may be pivotably, translationally, and/or slideably coupled to the elongate body 602, for example, at the second end 614. The second arm 610 may include a lateral end 658 and a medial end 660, as illustrated in FIG. 7B. The second arm 610 may also include a superior surface 662 and an inferior surface (not shown) opposite of the superior surface 662. The lateral end 658 of the second arm 610 may be coupled to the elongate body 602. In some embodiments, the second arm 610 may include at least one protrusion on a superior and/or inferior surface thereof. For example, the second arm 610 may include a first (e.g., anterior) protrusion 664 and a second (e.g., posterior) protrusion 666 at the lateral end 658 thereof. As illustrated in FIGS. 7A-B, the first protrusion 664 may be configured to be received within the first groove 622. The second protrusion 666 may be configured to be received within the second groove 624. The second arm 610 may include corresponding first and second protrusions on the inferior surface thereof. These protrusions may be configured to be received within first and second grooves on the superior (e.g., inner) surface of the lower wall 617 of the elongate body 602. In use, those skilled in the art may appreciate that the protrusions 664, 666 may guide the second arm 610 along the path defined by the grooves 622, 624, and may enable the second arm 610 to pivot relative thereto. The second arm 610 may include curved or angled anterior (e.g., inner) and/or posterior (e.g., outer) surfaces. For example, as illustrated in FIGS. 7A-B, the second arm 610 can include a curved anterior surface and an angled posterior surface. The second arm 610 may have a height that is not greater than the height of the elongate body 602. When the implant 600 is in the collapsed configuration, the second arm 610 may be configured to not protrude beyond the anterior and/or posterior side surfaces 620, 618 of the elongate body 602.

The first and second arms 608, 610 may be pivotably and/or hingedly coupled to each other. For example, the medial end 652 of the first arm 608 may be pivotably coupled to the medial end 660 second arm 610. As illustrated in FIGS. 7A-B, the medial end 652 of the first arm 608 may include a rounded (e.g., circular and/or cylindrical) hole 668. The rounded hole 668 may pass through the first arm 608 from the superior surface 662 to the inferior surface. The medial end 660 of the second arm 610 may include a pin 670. The pin 670 may be configured to be pivotably received within the rounded hole 668. In other embodiments, the first arm 608 may include a pin and the second arm 610 may include a rounded hole configured to pivotably receive the pin therein. Those skilled in the art may appreciate that the medial ends 652, 660 of the first and second arms 608, 610 may be configured to reversibly pivot towards and away from the elongate body 602. In the collapsed configuration, the medial ends 652, 660 may be pivoted towards the elongate body 602. In the expanded configuration, the medial ends 650, 660 may be pivoted away from the elongate body 602. The implant 600 may also include an expandable cavity 672. The expandable cavity 672 may be defined by the cutout 632 and the anterior surfaces of the first and second arms 608, 610. When in the expanded configuration, for example, as illustrated in FIG. 7B, the cavity 672 may be configured to receive bone growth material therein.

Embodiments herein are also directed to methods of installing the expandable spinal implant 600. These methods can include providing the expandable spinal implant 600 in the collapsed configuration, for example, as illustrated in FIG. 7A. When in the collapsed configuration, the medial ends 652, 660 of the first and second arms 608, 610 may be pivoted towards the elongate body 602.

In some embodiments, the step of providing the expandable spinal implant 600 in the collapsed configuration can include inserting the implant 600 into a selected location, such as a cavity between two vertebral bodies created by a discectomy or other procedure. In some embodiments, this step can include reversibly coupling the implant 600 to an insertion tool, and using the insertion tool to guide the implant 600 into the cavity. For example, in some embodiments, the insertion tool may threadably engage the receptacle 615 on the second end 614 of the implant 600. The implant 600 can be inserted into the cavity using a variety of approaches, such as anteriorly, posteriorly, transforaminally, or laterally. In some embodiments, the implant 600 may advantageously be configured to be inserted into an intervertebral space using a lateral procedure. Those skilled in the art may appreciate that, in some embodiments, when in the closed or collapsed configuration, the expandable spinal implant 600 may have a width that is about 50-65% less than the width in the expanded configuration. In some embodiments, the closed or collapsed width of the implant 600 may be about 55-60% less than the expanded width. In other embodiments, the closed or collapsed width of the implant 600 may be less than half of the expanded width thereof. Advantageously, the implant 600 may be inserted through a smaller, less-invasive opening that may result in reduced trauma to muscles, nerves, or other tissue. When used in a lateral procedure (e.g., lateral lumbar interbody fusion), the implant 600 may be inserted laterally in the far anterior side of the intervertebral space. This technique can advantageously reduce or minimize interaction with the posteriorly-located lumbar plexus.

Methods of installing the implant 600 can also include translating the lateral ends 650, 658 of the first and second arms 608, 610 medially (e.g., towards the center of the implant 600 and/or away from the first and second ends 612, 614). In some embodiments, this step can include translating the translatable connector 606 towards the second end 614 of the elongate body 602. Those skilled in the art may appreciate that as the connector 606 translates towards the second end 614, the first arm 608 may also be translated towards the second end 614, e.g., along the groove 626. The medial end 652 may also be urged away from the elongate body 602 as the first arm 608 pivots about the post disposed within the slot 648, as illustrated in FIG. 7B. As the medial end 652 of the first arm 608 is urged away from the elongate body 602, the medial end 652 may also urge the medial end 660 of the second arm 610 away from the elongate body 602. The second arm 610 may simultaneously travel medially and pivot within the grooves 622, 624 away (e.g., posteriorly) from the elongate body 602. The lateral ends 650, 658 of the first and second arms 608, 610 may be translated medially and/or the medial ends 652, 660 may be pivoted away from the elongate body 602 until the implant 600 attains an expanded width that is greater than the collapsed width. In some embodiments, the first and/or second arms 608, 620 are translated and/or pivoted until one or both are in contact with the apophyseal ring of a vertebra, as illustrated in FIG. 7C.

In some embodiments, the step of translating the lateral ends 650, 658 medially and simultaneously pivoting the medial ends 652, 660 away from the elongate body 602 may include actuating (e.g., rotating) the actuator 604. As the actuator 604 rotates, the threaded section may engage the threads on the translatable connector 606, urging the translatable connector 606 to translate along the actuator 604 towards the leading and/or trailing ends 603, 605 of the implant 600. In some embodiments, the actuator 604 may be actuated by a driver, such as an expansion driver. The driver may include a drive member configured to mate with the tool-engaging surface 636. For example, the driver may include a hexagonal, star, Phillips, and/or slotted drive member. In some embodiments, at least a portion of the driver may be inserted through the insertion tool, into the passageway 630, and into engagement with the actuator 604. Torque applied to the driver may then be transferred to the implant 600 through the actuator 604 as described herein.

In some embodiments, the method can further include locking or securing the expandable implant 600 in the expanded configuration. In other embodiments, the expandable implant 600 may be self-locking. For example, the threaded engagement between the actuator 604 and the translatable connector 606 may advantageously inhibit inadvertent lateral movement of the translatable connector 606.

Some methods can further include disengaging the insertion tool and/or driver from the implant 600. This step can include disengaging the driver from the actuator 604, for example, by retracting the driver away from the tool-engaging surface 636. This step can also include unthreading the insertion tool from the threaded receptacle 615. Methods herein can also include inserting bone graft material into the cavity 672. In some embodiments, this step may be accomplished before the insertion tool and/or driver is disengaged from the implant 600. In these embodiments, the insertion tool and/or driver may include a cannula through which the bone graft material may be transported to the implant 600, for example, via the passageway 628. In other embodiments, the bone graft material may be inserted after the insertion tool and/or driver is removed. In these embodiments, the bone graft material may be inserted, e.g., directly through the passageway 628 and/or through a graft window on the elongate body 602.

Turning now to FIGS. 8A-D, some embodiments herein are directed to an expandable spinal implant 800 that can include an elongate body 802, a first (e.g., leading) arm 804, and a second (e.g., trailing) arm 806. The expandable spinal implant 800 may include a length defined between a leading end 803 and a trailing end 805. The expandable implant 800 may also include a width defined from anterior side surface 808 of the elongate body 802 to a lateral end of the first and/or second arms 804, 806. The expandable spinal implant 800 may advantageously be configured to transition reversibly between an expanded configuration and a collapsed configuration. The implant 800 may have a width in the expandable configuration that is greater than a width in the collapsed configuration. In some embodiments, the implant 800 may have a collapsed width in the range of from about 10 mm to about 15 mm, and an expanded width in the range of from about 25 mm to about 30 mm.

As illustrated in FIG. 8B, the elongate body 802 can include a first (e.g., leading) end 810 and a second (e.g., trailing) end 812. The elongate body 802 may have a length as measured between the first end 810 and the second end 812. The second end 812 may be configured to engage an insertion tool. The second end 812 may include a receptacle (not shown) configured to engage the insertion tool. As illustrated in FIG. 8C, the elongate body 802 may include an upper wall 816, a lower wall 818 opposite the upper wall, a posterior side surface 822, and an anterior side surface 808. Those skilled in the art may appreciate that these and other directional terms herein are used for descriptive purposes and do not limit the orientation in which any of the expandable spinal implants described herein may be used. The elongate body 802 may have a width as measured between the anterior side surface 808 and the posterior side surface 822. In some embodiments, the width of the elongate body 802 may be generally equal to the width of the implant 800 in the collapsed configuration. In some embodiments, the elongate body 802 may include a cutout (not shown) that passes through the upper wall 816, lower wall 818, and/or posterior side surface 822. The may define a posterior opening along the posterior side surface 822. In some embodiments, the anterior side surface 808 may be convex, as viewed, for example, from the upper wall 816 and/or lower wall 818. The upper and/or lower walls 816, 818 may extend between the first end 810 and the second end 812. The elongate body 802 may be at least partially hollow. The upper wall 816 may include a superior (e.g., outer) and/or inferior (e.g., inner) surface. The lower wall 818 may also include a superior (e.g., inner) surface and/or an inferior (e.g., outer) surface. As described herein, the outer surfaces of the upper and/or lower walls 816, 818 may include a plurality of texturizing members. In some embodiments, the outer surfaces of the upper and/or lower walls 816, 818 may be convex, as viewed from the anterior side surface 808, posterior side surface 822, leading end 810, and/or trailing end 812. In other embodiments, the outer surfaces of the upper and/or lower walls 816, 818 may be angled and/or slanted, such that the height of the elongate body 802 is greater at the anterior side surface 808 than at the posterior side surface 822. In these embodiments, the expandable spinal implant 800 may be wedge-shaped. In other embodiments, the expandable spinal implant 800 may have a constant height.

In some embodiments, the elongate body 802 may be tapered at the leading end 810. For example, the leading end 810 can include a tapered height (e.g., as measured between the outer surfaces of the upper wall 816 and the lower wall 818) and/or a tapered width (e.g., as measured between the anterior side surface 808 and the posterior side surface 822). In use, the tapered leading end 810 may advantageously be configured to distract tissue during insertion.

The inferior surface of the upper wall 816 and/or the superior surface of the lower wall 818 can include one or more guide members (e.g., a groove, channel, rail, slot, track, and/or rack). In some embodiments, the guide member may include teeth, e.g., gear teeth and/or ratcheting. In some embodiments, the guide member(s) on the upper wall 816 may be parallel and/or symmetrical to the guide member(s) on the lower wall 818. The guide member(s) may include straight and/or curved sections. The guide member(s) may extend generally along a portion of the length of the elongate body 802. The guide member(s) may have a first end closer to the leading end 810 and a second end closer to the trailing end 812. Additionally, one end may be oriented anteriorly or posteriorly to the other end. In some embodiments, one or more guide members can be located at the leading and/or trailing ends 810, 812. For example, the inferior surface of the upper wall 816 can include at least one guide member at the leading end 810 and at least one guide member at the trailing end 812. The superior surface of the lower wall 818 may also include at least one guide member at the leading end 810 and at least one guide member at the trailing end 812. In some embodiments, the guide member at the leading end and the guide member at the trailing end may be symmetrical. In some embodiments, the inferior surface of the upper wall 816 can include a first groove (not shown) at the leading end 810 and a second groove 824 at the trailing end 812, as illustrated in FIG. 8D. The groove 824 can include a first (e.g., medial) end 864 and a second (e.g., lateral) end 866. The medial end 864 may be posterior to the lateral end 866.

In some embodiments, the elongate body 802 may have a generally constant width. In other embodiments, the width of the trailing end 812 may be generally equal to the width of the leading end 810. The elongate body 802 may include a passageway 826 extending at least partially along a length thereof. The passageway 826 may also include an opening 828 at the trailing end 812 of the elongate body 802, as illustrated in FIG. 8C. The passageway 826 may be configured to receive a tool, such as a driver, therethrough. In some embodiments, the passageway 826 may include a locking member, such as a pin, configured to restrain the tool therein. In some embodiments, the passageway 826 may be cylindrical (e.g., may include a constant, circular diameter). The passageway 826 may pass between (e.g., may not intersect) the upper and lower walls 816, 818. In some embodiments, the passageway 826 may intersect one or more additional passageways of the implant 800. For example, in embodiments where the elongate body 802 includes a cutout as described herein, the passageway 826 may be in fluid communication with the cutout. In some embodiments, the first and/or second arms 804, 806 may be accessible through the passageway 826. The trailing end 812, or other portion of the elongate body 802, may also include one or more windows configured to receive bone growth material therethrough.

The second arm 806 may be pivotably, translationally, and/or slideably coupled to the elongate body 802, for example, at the second end 812. As illustrated in FIG. 8D, the second arm 806 may include a lateral end 838 and a medial end 840. The second arm 806 may also include a superior surface 842 and an inferior surface (not shown) opposite of the superior surface 842. In some embodiments, the second arm 806 may be a unitary body. In other embodiments, the second arm 806 may include multiple pieces or segments. In some embodiments, the medial end 840 may be configured to be coupled with the second collar, described further herein. For example, the medial end 840 may include a rounded through hole 844 configured to receive a pin 846 associated and/or integrated with the second collar therethrough.

The medial end 840 of the second arm 806 may be coupled to the elongate body 802. In some embodiments, the second arm 806 may include at least one protrusion (e.g., bump, tab, and/or gear member) on a superior and/or inferior surface thereof. For example, the second arm 806 may include protrusion 848 on the superior surface 842 at the medial end 840 thereof. The protrusion may be configured to engage and/or mate with one of the guide members on the elongate body 802. As illustrated in FIG. 8D, the protrusion 848 may be configured to be received within the groove 824 at the second end 812 of the elongate body 802. The second arm 806 may include another protrusion on the inferior surface at the medial end 840 thereof. This protrusion may be configured to be received within a groove on the superior (e.g., inner) surface of the lower wall 818 of the elongate body 802. In use, those skilled in the art may appreciate that the protrusion 848 (alone or in combination with one or more protrusions on the inferior surface) may guide the second arm 806 along the path defined by the groove 824, and may enable the second arm 806 to pivot relative thereto, as illustrated in FIG. 8D. Additionally, those skilled in the art may appreciate that in other embodiments, the elongate body 802 may include one or more protrusions and the first and/or second arms 804, 806 may include one or more guide members. The second arm 806 may include a curved or angled anterior (e.g., outer) and/or posterior (e.g., inner) surface. The second arm 806 may have a height that is not greater than the height of the elongate body 802. When the implant 800 is in the collapsed configuration, the second arm 806 may be configured to not protrude beyond the anterior and/or posterior side surfaces 808, 822 of the elongate body 802, as illustrated in FIG. 8A.

The first arm 804 may be pivotably, translationally, and/or slideably coupled to the elongate body 802, for example, at the first end 810. As illustrated in FIG. 8A, the first arm 804 may include a lateral end 832 and a medial end 834. The first arm 804 may also include a superior surface 836 and an inferior surface (not shown) opposite the superior surface 836. In some embodiments, the first arm 804 may be a unitary body. In other embodiments, the first arm 804 may include multiple pieces or segments. In some embodiments, the medial end 834 may be configured to be coupled with the first collar, described further herein. For example, the medial end 834 may include a rounded through hole configured to receive a pin associated and/or integrated with the first collar therethrough.

The medial end 834 of the first arm 804 may be coupled to the elongate body 802. In some embodiments, the first arm 804 may include at least one protrusion (e.g., bump, tab, and/or gear member) on a superior and/or inferior surface thereof. For example, the first arm 804 may include a protrusion on the superior surface 836 at the medial end 834 thereof. The protrusion may be configured to engage and/or mate with one of the guide members on the elongate body 802. The protrusion may be configured to be received within a groove at the first end 810 of the elongate body 802. The first arm 804 may include another protrusion on the inferior surface at the medial end 834 thereof. This protrusion may be configured to be received within a groove on the superior (e.g., inner) surface of the lower wall 818 of the elongate body 802. In use, those skilled in the art may appreciate that the protrusion (alone or in combination with one or more protrusions on the inferior surface) may guide the first arm 804 along the path defined by the groove, and may enable the first arm 804 to pivot relative thereto. Additionally, those skilled in the art may appreciate that in other embodiments, the elongate body 802 may include one or more protrusions and the first and/or second arms 804, 806 may include one or more guide members. The first arm 804 may include a curved or angled anterior (e.g., outer) and/or posterior (e.g., inner) surface. The first arm 804 may have a height that is not greater than the height of the elongate body 802. When the implant 800 is in the collapsed configuration, the first arm 804 may be configured to not protrude beyond the anterior and/or posterior side surfaces 808, 822 of the elongate body 802, as illustrated in FIG. 8A.

In some embodiments, the expandable spinal implant 800 may further include a first collar 850 and/or a second collar 852, as illustrated in FIG. 8A. In some embodiments, the first collar 850 may include a distal end disposed within the passageway 826 and a proximal end configured to engage the first arm 804. The distal end may include a threaded hole extending therethrough and configured to be coaxial with the passageway 826. The proximal end may include a pin configured to be received within a through hole on the first arm 804, as described herein with respect to second arm 806. In other embodiments, the proximal end may include a through hole configured to be coaxial with the through hole on the first arm 804, and a separate pin may couple the first collar 850 and the first arm 804. In some embodiments, the first arm 804 may be in pivotable engagement with the first collar 850. The second collar 852 may include some or all of the same features as the first collar 850. As illustrated in FIG. 8A, the second collar 852 may be configured to engage the second arm 806 (e.g., at the medial end 840 thereof).

As illustrated in FIG. 8A, the implant 800 may also include an elongate rod 830. The elongate rod 830 may be configured to be housed and/or disposed within the passageway 826 of the elongate body 802, for example, as illustrated in FIG. 8A. The elongate rod 830 may be configured to rotate within the passageway 826 about longitudinal axis 858, illustrated in FIG. 8C. The elongate rod 830 may include a leading end 854 and a trailing end 856, as illustrated in FIG. 8C. The trailing end 856 may include a tool-engaging surface configured to engage a driver. For example, the trailing end 856 may include a socket configured to couple with a driver, such as a hexagonal, star, Phillips, and/or slotted driver. As illustrated in FIG. 8A, the elongate rod 830 may include a first threaded section 860 and a second threaded section 862 between the leading and trailing ends 854, 856. The threads of the first section 860 may extend in a direction opposite the threads of the second section 862 (e.g., clockwise and counterclockwise, or vice versa). The first threaded section 860 may be configured to engage the first collar 850 and the second threaded section may be configured to engage the second collar 852. In some embodiments, the elongate body 802 may include at least one retention member, such as a pin or keyed hole, which may be configured to inhibit translation of the elongate rod 830 within the passageway 826. In some embodiments, the elongate rod 830 may include a receptacle, such as a circumferential groove or undercut, that may be configured to receive or engage the retention member.

Embodiments herein are also directed to methods of installing the expandable spinal implant 800. These methods can include providing the expandable spinal implant 800 in the collapsed configuration, for example, as illustrated in FIG. 8A. When in the collapsed configuration, the lateral ends 832, 838 of the first and second arms 804, 806 may be pivoted towards the elongate body 602. Accordingly, the first and second arms 804, 806 may be generally parallel to the elongate body 602.

In some embodiments, the step of providing the expandable spinal implant 800 in the collapsed configuration can include inserting the implant 800 into a selected location, such as a cavity between two vertebral bodies created by a discectomy or other procedure. In some embodiments, this step can include reversibly coupling the implant 800 to an insertion tool, and using the insertion tool to guide the implant 800 into the cavity. The implant 800 can be inserted into the cavity using a variety of approaches, such as anteriorly, posteriorly, transforaminally, or laterally. In some embodiments, the implant 800 may advantageously be configured to be inserted into an intervertebral space using a lateral procedure. Those skilled in the art may appreciate that, in some embodiments, when in the closed or collapsed configuration, the expandable spinal implant 800 may have a width that is about 50-65% less than the width in the expanded configuration. In some embodiments, the closed or collapsed width of the implant 800 may be about 55-60% less than the expanded width. In other embodiments, the closed or collapsed width of the implant 800 may be less than half of the expanded width thereof. Advantageously, the implant 800 may be inserted through a smaller, less-invasive opening that may result in reduced trauma to muscles, nerves, or other tissue. When used in a lateral procedure (e.g., lateral lumbar interbody fusion), the implant 800 may be inserted laterally in the far anterior side of the intervertebral space. This technique can advantageously reduce or minimize interaction with the posteriorly-located lumbar plexus.

Methods of installing the implant 800 can also include translating the lateral ends 832, 838 of the first and second arms 804, 806 laterally and/or posteriorly (e.g., away from the center of the implant 800). In some embodiments, this step can include translating the first collar 850 towards the first end 810 of the elongate body 802 and translating the second collar 852 towards the second end 812. Those skilled in the art may appreciate that as the second collar 852 translates towards the second end 812, the second arm 806 may also be translated towards the second end 812, e.g., along the groove 824. The lateral end 838 may also be urged away from the elongate body 802 as the second arm 806 pivots about the pin 846, as illustrated in FIG. 8D. As the lateral end 838 of the second arm 806 is urged away from the elongate body 802, the lateral end 832 of the first arm 804 may similarly be urged away from the elongate body 802 by the first collar 850. For example, the first arm 804 may simultaneously travel laterally and pivot away (e.g., posteriorly) from the elongate body 802.

In embodiments where the expandable spinal implant 800 includes the elongate rod 830, the step of simultaneously translating and pivoting the lateral ends 832, 838 laterally and away from the elongate body 802 can include rotating the elongate rod 830. As the elongate rod 830 rotates, the first collar 850 may translate along the elongate rod 830 in a first direction, e.g., towards the leading end 810 of the elongate body 802. Additionally, the second collar 852 may translate along the elongate rod 830 in a second direction, e.g., towards the trailing end 812 of the elongate body 802. The first collar 850 may urge the first arm 804 to translate in the first direction and the second collar 852 may urge the second arm 806 to translate in the second direction. As the first arm 804 translates towards the leading end 810, one of the guide members (e.g., a groove or track) may guide the lateral end 832 of the first arm 804 to pivot away from the elongate body 802 (e.g., posteriorly). Similarly, as the second arm 806 translates towards the trailing end 812, the protrusion 848 may travel along the groove 824 of the elongate body 802, e.g., from the medial end 864 to the lateral end 866. The path defined by the groove 824 may guide the lateral end 838 of the second arm 806 away from the elongate body 802 (e.g., posteriorly), as illustrated in FIG. 8D. In some embodiments, the path defined by the elongate rod 830 and the first and second collars 850, 852, and the path defined by the guide members, may influence the paths taken by the first and second arms 804, 806. Those skilled in the art may appreciate that the first and second arms 806 may each be configured to rotate or pivot relative to the respective collars and guide members with which they may be engaged. The elongate rod 830 may be rotated, urging the lateral ends 832, 838 of the first and second arms 804, 806 away from the elongate body 802, until the implant 800 attains a second, expanded width that is greater than the closed or collapsed width, as illustrated in FIG. 8B. In some embodiments, the first and/or second arms 804, 806 may be translated and/or pivoted until one or both are in contact with the apophyseal ring of a vertebra. As illustrated in FIG. 8B, as the first and second arms 804, 806 translate laterally and/or posteriorly, they may define a cavity 868 therebetween.

In some embodiments, the elongate rod 830 can be rotated and/or actuated by a driver, such as an expansion driver. The driver may be part of the insertion tool. The driver may include a drive member configured to mate with a tool-engaging surface at the trailing end 856 of the elongate rod 830. For example, the driver may include a hexagonal, star, Phillips, and/or slotted drive member. In some embodiments, the driver may engage the elongate rod 830 by inserting the drive member (e.g., a hex key) into a socket at the trailing end 856 of the elongate rod 830. Torque may then be applied to the driver, thereby rotating the elongate rod 830.

In other embodiments, the expandable spinal implant 800 may not include elongate rod 830. In these embodiments, the implant 800 can be expanded using a driver (not shown). The driver can include an elongate rod assembly that can include a leading end, a trailing end, a first threaded section between the leading and trailing ends, and a second threaded section between the leading and trailing ends. In some embodiments, he threads of the first section can extend in a direction opposite the threads of the second section (e.g., clockwise and counterclockwise, or vice versa). In other embodiments, they can extend in the same direction. Methods of installing the expandable spinal implant 800 can include providing the implant in the collapsed configuration as described herein and inserting the driver into the passageway 826. The methods can also include coupling the first threaded section of the elongate rod assembly with the first collar 850 and coupling the second threaded section of the elongate rod assembly with the second collar 852. The driver can also be coupled to the elongate body 802, for example, to inhibit longitudinal translation of the driver. The methods can also include rotating the elongate rod assembly, thereby translating the first collar 850 in a first direction and the second collar 852 in a second, opposite direction, and consequently urging the lateral ends 832, 838 of the first and second arms 804, 806 laterally and/or posteriorly until the implant 800 attains an expanded width that is greater than the collapsed width.

In some embodiments, the elongate rod assembly can include a first rod member concentrically disposed within a cannula of a second rod member. The first threaded section may be disposed on the first rod member and the second threaded section may be disposed on the second rod member. The first rod member may be configured to extend and retract from within the second rod member. The first and second rod members may be configured to rotate independently of each other. In these embodiments, the step of rotating the elongate rod assembly can include rotating the first rod member to translate the first collar 850 in a first direction (e.g., towards the leading end 803) and rotating the second rod member to translate the second collar 852 in a second direction (e.g., towards the trailing end 805).

In some embodiments, the method can further include locking or securing the expandable implant 800 in the expanded configuration. This step can include threading a set screw into the implant 800 to block or prevent the first and/or second arms 804, 806 from retracting to their collapsed positions. In other embodiments, one or more components of the implant 800 may include a retention member, such as a ratchet or angled tooth, which may be configured to prevent the first and/or second arms 804, 806 from retracting. In yet other embodiments, the implant 800 may be self-locking. For example, the threaded engagement between the elongate rod 830 and the first and second collars 850, 852 may advantageously inhibit inadvertent lateral movement of the first and second collars 850, 852.

Some methods herein can further include disengaging the insertion tool and/or driver from the implant 800. In embodiments that include the elongate rod 830, this step can include disengaging the driver from the elongate rod 830 (e.g., retracting the driver from the trailing end 856). In embodiments that do not include the elongate rod 830, this step can include disengaging (e.g., unthreading) the driver from the first and second collars 850, 852. This step can also include disengaging the insertion tool from the receptacle at the second end 812. Methods herein can also include inserting bone graft material into the cavity 868. In some embodiments, this step may be accomplished before the insertion tool and/or driver is disengaged from the implant 800. In these embodiments, the insertion tool and/or driver may include a cannula through which the bone graft material may be transported to the implant 800, for example, via the passageway 826. In other embodiments, the bone graft material may be inserted after the insertion tool and/or driver is removed. In these embodiments, the bone graft material may be inserted, e.g., through the passageway 826 and/or through a graft window on the elongate body 802.

In some embodiments, one or more of the expandable spinal implants discussed above can be used with graft material inserted therein as part of a fusion procedure. In addition, the expandable spinal implants can be used with other implants as part of a system, including stabilizing rods, screws (e.g., pedicle screws), hooks, and other fusion devices. In some embodiments, the expandable spinal implants can be used in conjunction with prosthetic devices, such as an artificial disc. For example, an expandable spinal implant can be used on one spinal level, while a prosthetic implant can used on a different spinal level.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:

1. A laterally expanding intervertebral spacer comprising:
a body having a leading end, a trailing end, an upper wall adapted to contact a lower surface of a vertebral body and a lower wall adapted to contact an upper surface of an adjacent vertebral body;
a first arm having a first end pivotally and translatably coupled to the body and a second end;
a second arm having a first end pivotally and translatably coupled to the body and a second end;
an actuator for laterally extending the second ends of the first and second arms and a translating connector coupled between the actuator and the first arm, and adapted to translate relative to the actuator, wherein the body includes an elongate recess and the first arm has a protrusion received in the elongate recess for rotation and translation relative to the body when the translating connector translates relative to the actuator.

2. The spacer of claim 1, wherein the second ends of the first and second arms are pivotally coupled to each other such that extension of the second end of the first arm by the actuator simultaneously causes extension of the second end of the second arm.

3. The spacer of claim 1, wherein:
the actuator includes an external threading;
the translating connector includes an external thread section in mesh with the external threading of the actuator such that rotation of the actuator causes translation of the translating connector.

4. The spacer of claim 1, wherein the translating connector includes a vertical slot and the first arm includes a post received in the vertical slot of the translating connector.

5. The spacer of claim 1, wherein the body includes an internal passage and one end of the actuator includes a tool engaging surface to receive a driver through the internal passage for actuating the actuator.

6. The spacer of claim 1, wherein the body includes first and second grooves and the second arm has first and second protrusions respectively received in the first and second grooves.

7. The spacer of claim 6, wherein a distance between the first and second grooves decreases in a direction away from the trailing end and toward the leading end.

8. The spacer of claim 1, wherein the actuator has a circumferential groove, further comprising a pair of pins disposed in the circumferential groove to prevent translation of the actuator.

9. A laterally expanding intervertebral spacer comprising:
an elongate body having a trailing end and a leading end and a cutout therebetween;
a first arm having a first end pivotally and translatably coupled to the body and a second end;
a second arm having a first end pivotally and translatably coupled to the body and a second end pivotally coupled to the second end of the first arm;
wherein the second ends of the first and second arm are disposed in the cutout in a contracted state;
an actuator for laterally extending the second ends of the first and second arm in an expanded state, wherein the first and second arms laterally expand by rotation and translation of both the first and second arms; and
a translating connector coupled between the actuator and the first arm, and adapted to translate relative to the actuator, wherein the body includes an elongate recess and the first arm has a protrusion received in the elongate recess for rotation and translation relative to the body when the translating connector translates relative to the actuator.

10. The spacer of claim 9, wherein the second ends of the first and second arms are pivotally coupled to each other through a pivotal pin received in respective holes of the first and second arms.

11. The spacer of claim 9, wherein:
the actuator includes an external threading;

the translating connector includes an external thread section in mesh with the external threading of the actuator such that rotation of the actuator causes translation of the translating connector.

12. The spacer of claim 9, wherein the translating connector includes a vertical slot and the first arm includes a post received in the vertical slot of the translating connector.

13. The spacer of claim 9, wherein the body includes an internal passage and one end of the actuator includes a tool engaging surface to receive a driver through the internal passage for actuating the actuator.

14. The spacer of claim 9, wherein the body includes first and second grooves and the second arm has first and second protrusions respectively received in the first and second grooves.

15. The spacer of claim 14, wherein a distance between the first and second grooves decreases in a direction away from the trailing end and toward the leading end.

16. The spacer of claim 9, wherein the actuator has a circumferential groove, further comprising a pair of pins disposed in the circumferential groove to prevent translation of the actuator.

* * * * *